US011517248B2

(12) United States Patent
Myers et al.

(10) Patent No.: US 11,517,248 B2
(45) Date of Patent: Dec. 6, 2022

(54) AMBULATORY SEIZURE MONITORING SYSTEM AND METHOD

(71) Applicant: UNIVERSITY OF TENNESSEE RESEARCH FOUNDATION, Knoxville, TN (US)

(72) Inventors: Mark Hebron Myers, Germantown, TN (US); Karl Arthur Sillay, Germantown, TN (US); John Douglas Birdwell, Oak Ridge, TN (US)

(*) Notice: Subject to any disclaimer, the term of this patent is extended or adjusted under 35 U.S.C. 154(b) by 441 days.

(21) Appl. No.: 16/081,511

(22) PCT Filed: Mar. 3, 2017

(86) PCT No.: PCT/US2017/020674
§ 371 (c)(1),
(2) Date: Aug. 31, 2018

(87) PCT Pub. No.: WO2017/152059
PCT Pub. Date: Sep. 8, 2017

(65) Prior Publication Data
US 2019/0059803 A1 Feb. 28, 2019

Related U.S. Application Data

(60) Provisional application No. 62/303,715, filed on Mar. 4, 2016.

(51) Int. Cl.
*A61B 5/00* (2006.01)
*A61B 5/369* (2021.01)
(52) U.S. Cl.
CPC ............ *A61B 5/4094* (2013.01); *A61B 5/369* (2021.01); *A61B 5/746* (2013.01); *A61B 5/0006* (2013.01); *A61B 5/7275* (2013.01); *A61B 5/743* (2013.01)

(58) Field of Classification Search
CPC ..... A61B 5/4094; A61B 5/0476; A61B 5/746; A61B 5/0006; A61B 5/7275; A61B 5/743
USPC ........................................................ 600/544
See application file for complete search history.

(56) References Cited

U.S. PATENT DOCUMENTS 5,564,433 A * 10/1996 Thornton ............. A61B 5/0476
600/544
2003/0004428 A1 1/2003 Pless et al.
2009/0281446 A2 11/2009 Ludving et al.
(Continued)

OTHER PUBLICATIONS

Myers, Mark H., and Robert Kozma. "Seizure prediction through dynamic synchronization measures of neural populations." 2009 International Joint Conference on Neural Networks. IEEE, 2009 (Year: 2009).*

(Continued)

*Primary Examiner* — Alex M Valvis
*Assistant Examiner* — Chanel J Jhin
(74) *Attorney, Agent, or Firm* — Thomas|Horstemeyer, LLP

(57) ABSTRACT

One embodiment of an exemplary ambulatory seizure monitoring method calculates a phase lock value synchrony level of a neurological signal of an individual; detects an onset of a seizure event for the individual by comparing the phase lock value synchrony level with a patient threshold for the individual; and transmits a notification to a remote communication device indicating the onset of the seizure event for the individual.

22 Claims, 19 Drawing Sheets

(56) References Cited

U.S. PATENT DOCUMENTS

2011/0153704 A1* 6/2011 Toraichi ............ H03H 17/0229
708/300
2011/0270095 A1* 11/2011 Bukhman .............. A61B 5/349
607/45
2012/0197092 A1 8/2012 Luo et al.

OTHER PUBLICATIONS

International Search Report and Written Opinion for PCT/US2017/020674, dated Aug. 1, 2017.
Abdelhalim et al. "Phase-Synchronization Early Epileptic Seizure Detector VLSI Architecture" In: IEEE Trans Biomed Circuits Syst. Oct. 2011; 5(5):430-8 [online] [retrieved on Jul. 11, 2017 (Jul. 11, 2017)].
Szczepanski et al. "Dynamic Changes in Phase-Amplitude Coupling Facilitate Spatial Attention Control in Franta-Parietal Cortex" In: PLoS Biol. Aug. 26, 2014 [online] [retrieved on Jul. 11, 2017 (Jul. 11, 2017)].
Miyers et al. "Seizure Prediction and Detection via Phase and Amplitude Lock Values" In: Frontiers in Human Neuroscience. Mar. 8, 2016; 10:80 [online] [retrieved on Jul. 11, 2017 (Jul. 11, 2017)].

\* cited by examiner

| Pat. No. | No. of Sz | Interictal hours | Sensitivity (%) | Precision (%) | FP/h | FP % | $p$-value |
|---|---|---|---|---|---|---|---|
| 1 (1) | 3 | 3 | 67 | 100 | 0.00 | 0.00 | 0.002 |
| 2 (2) | 3 | 3 | 33 | 33 | 1.11 | 66.67 | 0.031 |
| 3 (3) | 3 | 3 | 100 | 100 | 0.00 | 0.00 | 0.000 |
| 4 (5) | 3 | 3 | 67 | 100 | 0.00 | 0.00 | 0.000 |
| 5 (6) | 3 | 4 | 67 | 100 | 0.00 | 0.00 | 0.000 |
| 6 (11) | 3 | 3 | 67 | 100 | 0.00 | 0.00 | 0.092 |
| 7 (18) | 3 | 3 | 100 | 100 | 0.00 | 0.00 | 0.000 |
| 8 (20) | 3 | 3 | 67 | 50 | 0.56 | 33.33 | 0.211 |
| 9 (22) | 3 | 3 | 100 | 100 | 0.00 | 0.00 | 0.000 |
| 10 (24) | 3 | 3 | 100 | 100 | 0.00 | 0.00 | 0.000 |

FIG. 2G

Table 1. Electrode Settings

| Name | Description | Location |
|---|---|---|
| CH1+ / CH2+ | Positive channel | Forehead |
| CH1- / CH2- | Negative channel | Earlobe |
| DRL | Reference | Earlobe |

FIG. 4

| Filter Band (Hz) | | 1-12 | | 6-12 | | 12-20 | | 20-30 | | 30-40 | | 40-50 | |
|---|---|---|---|---|---|---|---|---|---|---|---|---|---|
| Window Size (samples) | | 1000 | 3000 | 1000 | 3000 | 1000 | 3000 | 1000 | 3000 | 1000 | 3000 | 1000 | 3000 |
| Patient | Implant* | | | | | | | | | | | | |
| 1 | Pre (1) | 1 | 1 | 1 | 1 | | | | | 1 | 1 | 1 | 1 |
| | Post (5) | 5 | 5 | 5 | 5 | 5 | 5 | 5 | 5 | 5 | 5 | 5 | 5 |
| 2 | Pre (4) | 2 | 1 | 3 | | | | | | | | 3 | 1 |
| | Post (5) | 4 | 2 | 5 | 2 | | | | | | | 2 | 1 |
| 3 | Pre (4) | 1 | | 2 | | | | | | 1 | | 2 | |
| | Post (5) | 4 | 3 | 1 | 4 | | | | | | | 2 | 4 |

*Number of actual seizures is given in parentheses

FIG. 9

| Filter Band (Hz) | | 1-12 | | 6-12 | | 12-20 | | 20-30 | | 30-40 | | 40-50 | |
|---|---|---|---|---|---|---|---|---|---|---|---|---|---|
| Window Size (samples) | | 1000 | 3000 | 1000 | 3000 | 1000 | 3000 | 1000 | 3000 | 1000 | 3000 | 1000 | 3000 |
| Patient | Implant* | | | | | | | | | | | | |
| 1 | Pre (1) | 1 | 1 | 1 | 1 | | | | | 1 | 1 | 1 | 1 |
| | Post (5) | 2 | | 4 | 1 | | | | | | | 3 | 1 |
| 2 | Pre (4) | 2 | 1 | | | | | | | | | 2 | 1 |
| | Post (5) | 4 | 2 | 5 | 2 | | | | | | | 2 | 1 |
| 3 | Pre (4) | 1 | | 2 | | | | | | | | 2 | |
| | Post (5) | 4 | 3 | 1 | 2 | | | | | | | 2 | 4 |

*Number of actual seizures is given in parentheses

FIG. 10

AMBULATORY SEIZURE MONITORING SYSTEM AND METHOD

CROSS-REFERENCE TO RELATED APPLICATION

This application is the National Stage of International Application No. PCT/US2017/020674, filed Mar. 3, 2017, which claims priority to U.S. provisional application entitled, "Ambulatory Seizure Monitoring Device," having Ser. No. 62/303,715, filed Mar. 4, 2016, now expired, which is entirely incorporated herein by reference.

TECHNICAL FIELD

The present disclosure is generally related to techniques for seizure prediction.

BACKGROUND

The brain, with billions of neurons and synapses, is the marvelous core of human thought, action, and memory. However, if neuronal activity manifests into abnormal electrical activity across the brain, neural behavior may exhibit synchronous neural firings known as seizures. If a patient repeatedly experiences unprovoked seizures, the patient may be diagnosed with epilepsy.

SUMMARY

Embodiments of the present disclosure provide systems and methods for ambulatory seizure monitoring techniques. Briefly described, in architecture, one embodiment of the system, among others, includes at least one computing device; and an application executable in the at least one computing device. The application, when executed, causes the at least one computing device to: receive a first series of electroencephalograph (EEG) signals from a first sensor and a second corresponding series of EEG signals from a second sensor, the first sensor and the second sensor positioned on a head of an individual; determine a phase lock value based at least in part on the first series of EEG signals and the second corresponding series of EEG signals; and transmit a notification to a remote communication device in response to at least in part a comparison of the phase lock value with a patient threshold indicating an onset of a seizure event for the individual.

Embodiments of such a system may further include the following features: the application further causes the at least one computing device to determine an amplitude lock value based at least in part on the first series of EEG signals and the second corresponding series of EEG signals, wherein the comparison comprises a first comparison, and transmitting the notification further comprises transmitting the notification in response to a second comparison of the amplitude lock value with the patient threshold; transmitting the notification further comprising transmitting the notification via a wireless transmitter to the remote communication device; the comparison indicates that the phase lock value exceeds the patient threshold for a time period; determining the phase lock value further comprises determining a measure of phase synchrony between the first EEG signal and the second EEG signal; and/or the patient threshold is based at least in part on previous EEG patient data associated with the individual; the first sensor and the second sensor are coupled to a cap worn on the head of the individual, among other features.

The present disclosure can also be viewed as providing methods for ambulatory seizure monitoring. In this regard, one embodiment of such a method, among others, can be broadly summarized by the following steps: applying a frequency filter to a first electroencephalograph (EEG) signal from a first sensor and a second EEG signal from a second sensor, the first sensor and the second sensor are positioned on a head of an individual; receiving, in at least one computing device, a first series of filtered EEG signals and a second corresponding series of filtered EEG signals; calculating, by the at least one computing device, a phase lock value synchrony level based at least in part on the first series of filtered EEG signals and the second corresponding series of filtered EEG signals; detecting, by the at least one computing device, an onset of a seizure event for the individual by comparing the phase lock value synchrony level with a patient threshold for the individual; and transmitting, by the at least one computing device, a notification to a remote communication device indicating the onset of the seizure event for the individual.

Embodiments of such a method may further include the following features: the second sensor is a reference EEG signal; the second sensor is positioned on a first ear of the individual and a third sensor is a ground reference, the third sensor being positioned on a second ear of the individual; the frequency filter passes frequencies from 0.1 Hz to 50 Hz that may be collected through sensors which may be dry active or passive electrodes; and/or the comparison indicates that the phase lock value exceeds the patient threshold for a time period.

An additional embodiment of a method of the present disclosure includes the operations of determining, from previously recorded neurological signals, a patient threshold for an individual that indicates an onset of a seizure event for the individual; affixing a plurality of electroencephalograph (EEG) sensors to a head of the individual; receiving, by a computing device, neurological signals from the EEG sensors affixed to the head of the individual; calculating, by the computing device, a phase lock value for the neurological signals over a time series; comparing, by the computing device, at least the phase lock value with the patient threshold; and responsive to the comparison, sending, by the computing device, a notification indicating the onset of the seizure event for the individual.

Embodiments of such a method may further include the following features: the patient threshold is identified by locating fast changes of phase values for the neurological signal; the notification is sent when the phase lock value exceeds the patient threshold; the notification is directed to a seizure control system, wherein the seizure control system is configured to deliver electrical simulation to a brain of the individual when the Phase Lock Value (PLV) rises above the patient threshold; calculating an amplitude lock value for the neurological signals over a time series; comparing the amplitude lock value with a patient threshold; and/or sending a notification when the phase lock value exceeds the patient threshold and the amplitude lock value exceeds the patient threshold Other systems, methods, features, and advantages of the present disclosure will be or become apparent to one with skill in the art upon examination of the following drawings and detailed description. It is intended that all such additional systems, methods, features, and advantages be included within this description, be within the scope of the present disclosure, and be protected by the accompanying claims.

BRIEF DESCRIPTION OF THE DRAWINGS

Many aspects of the present disclosure can be better understood with reference to the following drawings. The components in the drawings are not necessarily to scale, with emphasis instead being placed upon clearly illustrating the principles of the disclosure. Moreover, in the drawings, like reference numerals designate corresponding parts throughout the several views.

FIG. 2G is a table showing results from seizure prediction analysis of an exemplary embodiment of the present disclosure.

FIG. 4 is a table illustrating examples of various electrode settings, according to various embodiments of the present disclosure.

FIG. 9 is a table of a number of seizures detected pre-implant and post-implant per frequency band filter range and window size, according to various embodiments of the present disclosure.

FIG. 10 is a table of a number of seizures predicted pre-implant and post-implant per frequency band filter range and window size, according to various embodiments of the present disclosure.

DETAILED DESCRIPTION

Figure 1:
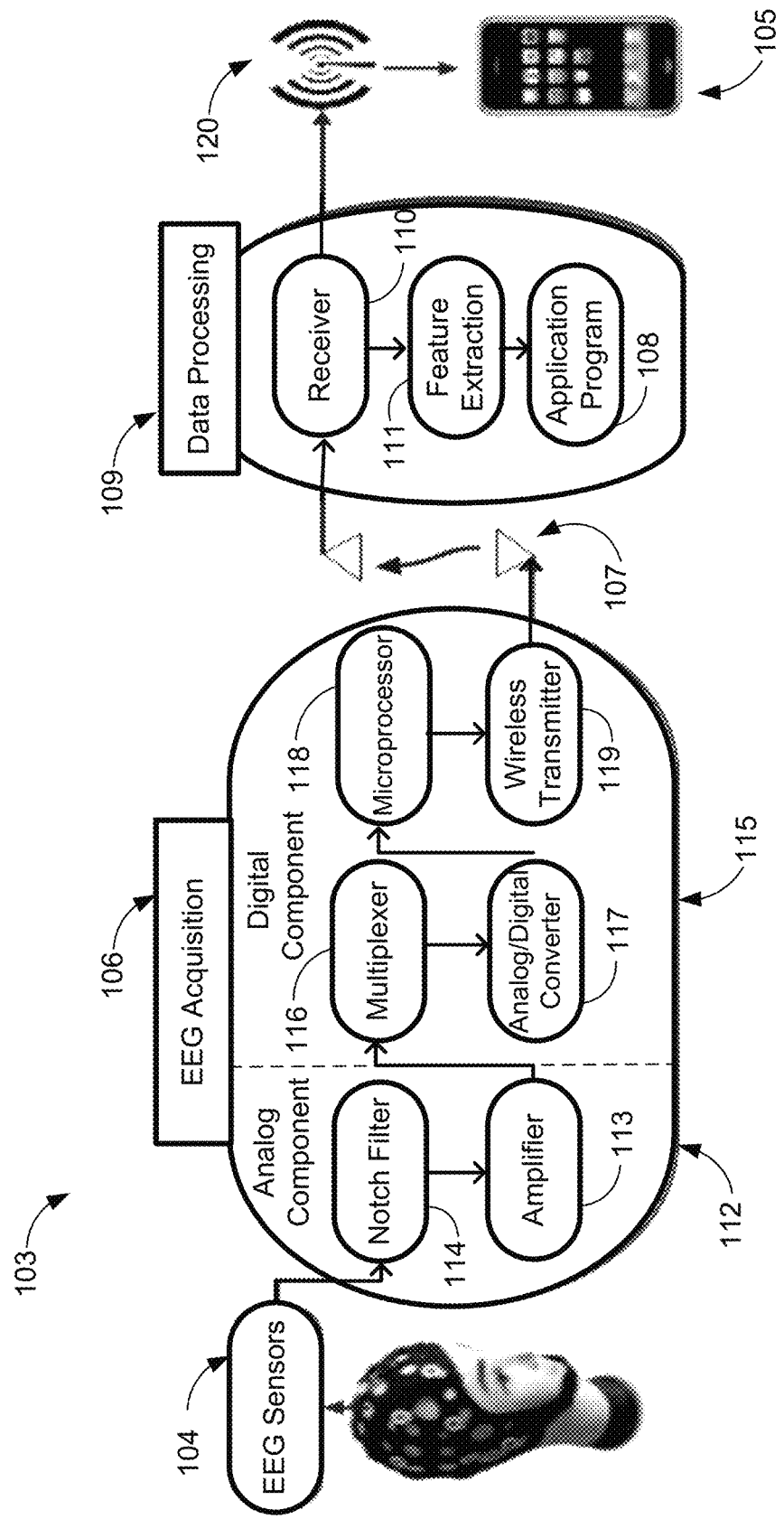
FIG. 1 is a schematic block diagram of an exemplary ambulatory seizure monitoring system comprising a wireless brain computer interface system communicating data to a mobile device, according to various embodiments of the present disclosure.

Seizure prediction based on electroencephalograms (EEG)/intracranial EEG (iEEG) is complicated by two factors. The first is that preictal and interictal EEG/iEEG patterns across patients vary substantially. There may be no single generic algorithm that can be applied to all patients and can achieve high sensitivity. The second is that EEG/iEEG is highly complex and varies over time, and no single measure of EEG/iEEG has yet been predictive on its own.

Seizure activity is characterized by recurrent, short-term electrical discharges of the cerebral cortex that result in intermittent disturbances of brain function. The state between seizures, known as interictal behavior, appears to have minor spiking activity. In seizures of focal onset (e.g., focal seizures and partial seizures), the anatomical distribution of the interictal spikes varies, but spikes tend to occur most commonly in the epileptogenic zone and its connections. During the seizure, organized, semi-periodic electrical discharges develop in the epileptogenic zone and spread, within seconds, over widespread areas of cerebral cortex.

Embodiments of the present disclosure utilize a patient-specific classification method based on multiple features extracted from EEG/iEEG. Seizure detection analysis in accordance with the present disclosure includes the testing of pre-ictal (pre-seizure) and seizure occurrences in order to take into consideration interictal events for testing false detection occurrences through instances where there are no impending seizures. In accordance with embodiments of the present disclosure, an approach to seizure prediction and detection can use phase lock values (PLV) and calculate the difference of phase between electroencephalograph (EEG) electrodes which are local and remote to the epileptic event. PLV can be used as the seizure prediction marker and can signify the emergence of abnormal neuronal activations through local neuron populations, or the epileptogenesis. Accordingly, an exemplary technique for identifying the seizure prediction marker involves locating the fast changes of phase and amplitude of the EEG signal.

In addition, various embodiments of the present disclosure relate to an enhanced seizure detection device that can calculate PLV from EEG data obtained from electrodes on the scalp of an individual and wirelessly communicate an alert to a communication device (e.g., smartphone or tablet) that is notified of a possible impending seizure event. For example, via the notification, a physician, emergency response system, family member, or designee of an impending seizure attack may be alerted of the possible impending seizure event. Other embodiments can provide can provide an alert mechanism by displaying and alerting the caretaker of the pending seizure attack, with vibration, audio alert or other designated method of the likelihood of seizure or presumed risk (via, for example, a communication device). The various embodiments of the present disclosure can serve as a safety monitor that can be used for post-event detection to obtain objective measurements that should correlate with the neurological status and health of the subject. A cap with EEG electrodes can be used for non-invasive EEG data collection. In some embodiments, an implantable detection system can be used to identify and generate an alert for an impending seizure.

The development of advanced EEG electrodes and signal processing technologies which measure brain signals precisely with low noise is an important challenge. Practically, the signal acquisition part of general wireless brain computer interface (BCI) systems only contains a signal acquisition circuit and a micro-processor based embedded system for transmission of the measured EEG signals. Dry electrodes can have a clear advantage over electrodes that need conductive gels or glues for installation, which can cause depreciation of the acquired EEG signal and irritation over time for the subject. Active electrodes can contain amplifier or buffer circuits integrated to the electrodes themselves. These amplifier or buffer circuits can be positioned between the electrodes and the signal acquisition front-end. They can match scalp impedance to the requirements of the EEG data acquisition system, providing high input impedance at the electrode-amplifier interface, while active circuits provide gain and attenuate noise. This is desired for dry electrodes that do not use conductive fluids. The low output impedance of the amplifier can eliminate artifacts caused by posture changes in mobile environments, maintaining the quality of measured physiological signals.

Turning to the drawings, a general description of embodiments of an ambulatory seizure monitoring system and its components is provided, followed by a discussion of the operation of the same. With reference to FIG. 1, shown is one embodiment, among others, of an ambulatory seizure monitoring system comprising a BCI system or device 103 that is composed of EEG data acquisition 106 and data processing components 109. In the analog front-end stage 112, amplifier 113 and bandwidth limiter circuits 114, such as notch filter, can be included to enable a robust and reliable acquisition of EEG signals from the sensitive raw signals. EEG sensors 104 (e.g. electrodes) can be adapted to receive these sensitive raw signals. Because the amplitude of EEG signals is small compared to the measurement of EEG signals directly from the cortex, pre-amplification of the measured EEG signals at the analog front-end 112 is important. In this amplification process/stage 113, wireless BCI systems typically use operational amplifiers or instrumentation amplifiers. High input impedance can be used to match scale impedance, and in these circumstances, it is expected that a gain on the order of $10^3$-$10^5$ may be needed to amplify sensed voltage levels on the order of 10 µV to levels on the order of 100 mV-1V for conversion by typical analog to digital converters (ADC) 117.

However, the precise amplification gain of the analog front-end 112 can depend on the components of the digital system 115. In some embodiments, a frequency filtering procedure is needed to remove various noise components. Seizure prediction frequencies found in EEG signals can occupy a narrow bandwidth, normally from 0.1 Hz to less than 50 Hz. Analog filtering can be used to remove DC signal components (e.g., using a low pass filter) and eliminate aliasing effects caused by the ADC 117 (e.g., using a high pass filter), while digital filtering can be used more efficiently to extract useful signals from the desired frequency bands. An analog filter (e.g., using a notch filter 114) can also be used to attenuate power line noise, particularly noise at 120 Hz and its harmonics, which is caused by inductive coupling from electrical devices such as fluorescent lighting to sensor leads. These filtering processes can be performed using active filtering circuits.

In the digital system stage 115 of the illustrated embodiment, four integrated circuits are included: a multiplexer 116, an ADC 117, a microprocessor 118, and a wireless transmission unit 119. Two or more circuits may be combined into a single integrated circuit or package using, for example, a FPGA, an ASIC, a custom IC, or a multi-chip module or package. A sigma-delta ADC can be effectively utilized to obtain a high-resolution digital signal and effect high-quality pass-band filtering in the digital domain. Most EEG-based wireless BCI systems support multi-channel recording. Simultaneous measurement of multi-channel signals can require multiple sample-and-hold circuits with low clock skew, and a multiplexer can be used to sample all of the channels using a single ADC. Given the low cost of sigma-delta ADC devices, however, it may be cost-effective to utilize multiple ADCs rather than a multiplexed solution. Methods well-known in the art can be utilized to synchronize ADC sampling when this is desired. The sampling frequency of the ADC 117 can be determined by the selected ADC, the speed of the microprocessor, the bandwidth available for wireless transmission, and frequency range of interest in the EEG signals.

The microprocessor 118 can pack the corrected EEG data into a packet buffer and transfer the buffer's content to the wireless transmission unit 119, using an alternate buffer while the transmission takes place. The microprocessor 118 can also manage the components of the entire system. The microprocessor 118 may be implemented using a library component (core) implemented in a FPGA. In some embodiments, the microprocessor 118 and wireless transmission unit(s) 119 can each be implemented primarily in a single integrated circuit, or package, with additional components to supply power and couple the signal to an antenna 107. These components can be implemented on a single circuit board module roughly the size of a pack of cards or smaller. Some wireless BCI systems load the feature extraction algorithm on the microprocessor 118 to process the EEG signals internally. Because the recorded multichannel EEG data are transmitted from the portable EEG acquisition device 106 to the host system, the wireless transmission unit 119 can be important in some embodiments. Considering various alternatives, Bluetooth has many advantages such as sufficient transmission rates and wide accessibility. Including the analog front-end 112 and digital system stage 115, the acquisition unit of wireless BCI systems generally operates using onboard power sources such as Li-ion, Li-polymer, and NiMH batteries. The data processing module 109 can comprise a receiving module or receiver 110 to intercept processed EEG signals from the EEG data acquisition module 106, seizure feature extraction module 111, and a user interface as part of an application program 108 to alert the user of the incoming seizure via a wireless transmission, from a radio link module (e.g., Bluetooth link) 120, to a communication device, such as mobile device 105, among others. The data processing component 109 can also transmit to the user and caregiver (e.g., to the user/caregiver's mobile device or to the user/caregiver's telephone system, such as a POTS telephone system) incoming seizure alerts so that they may be able to aid the seizure patient in managing his or her condition.

FIG. 1 illustrates the various individual components of the ambulatory seizure monitoring system as implemented in one embodiment, among others. In another embodiment, among others, the functionality associated with individual components can be designed in one or more integrated circuit components. For example, the functionality associated with various individual components can be embodied in dedicated hardware, a combination of software/general purpose hardware, or a combination of software/general purpose hardware and dedicated hardware. If embodied in dedicated hardware, each can be implemented as a circuit, core, or state machine that employs any one of or a combination of a number of technologies. These technologies may include, but are not limited to, discrete logic circuits having logic gates for implementing various logic functions upon an application of one or more data signals, application specific integrated circuits (ASICs) having appropriate logic gates, field-programmable gate arrays (FPGAs), or other components, etc. Such technologies are generally well known by those skilled in the art and, consequently, are not described in detail herein. In addition, in some embodiments, the data processing module 109 may be implemented on the mobile device, or on a device adapted to be worn by a human, such as a head band or cap, and may include the electrodes.

Figure 2A:
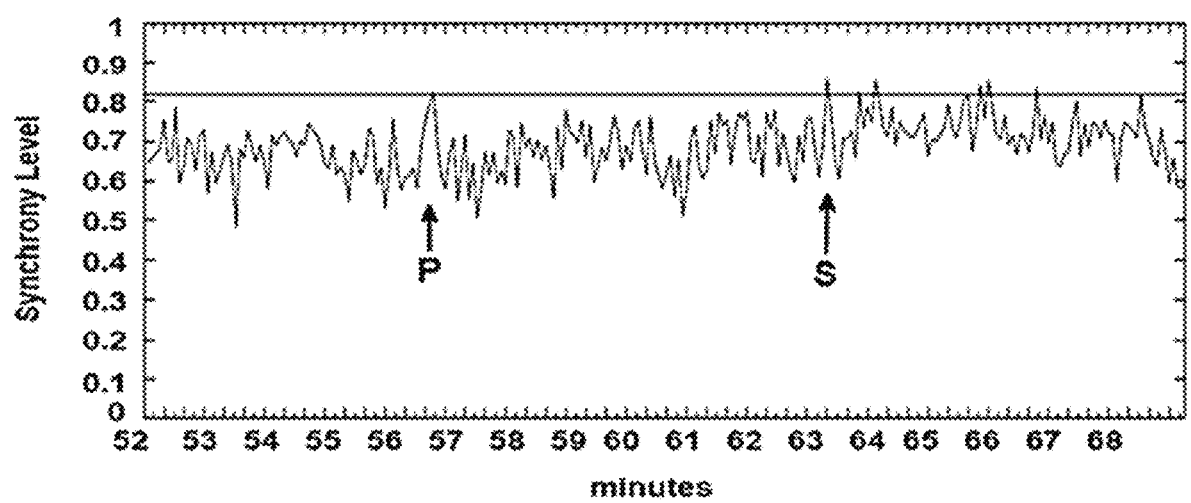
FIG. 2A is a graph illustrating an example of phase lock values over a time period for a patient, according to various embodiments of the present disclosure.

Referring now to FIG. 2A, phase synchronization or "locking" between neural populations does not occur by random chance. Phase synchronization occurs in the presence of the entrainment of neural populations. Neural populations exhibit a degree of noise that maintains independent basal activity, yet neural population synchronization can occur if a dominant waveform emerges from a local neural area. If there exists a strong coupling between neural populations, phase synchronization will propagate throughout the network, as seen in focal seizures that emerge into grand-mal seizures.

In accordance with the present disclosure, seizure feature extraction can be accomplished via a seizure prediction measurement which is implemented to determine when neurological signals across the scalp behave synchronously and align in movement. This measurement can be used to determine if EEG signals will either synchronize or operate independently.

On the y-axis of FIG. 2A, as the measured signal moves closer to a value of '1', the neurological signals are behaving in a synchronous manner, which corresponds to the signature behavior of seizure activity. As neurological signals synchronize, the measured signal will reach and/or cross a defined threshold signifying that a seizure is about to occur. After a period of time, the neurological signals will cross the threshold and appear closer to '1', signifying the brain has moved into the seizure state.

The various embodiments of the present disclosure use time series analysis techniques with respect to seizure prediction. EEG data are recorded from different electrode contacts. The mean phase coherence can be determined through phase lock value (PLV) calculations of the EEG data using a sliding window technique. The optimal threshold can be determined retrospectively as a customized patient stimulation signal. For a proper prediction, the alarm can be set within a proper distance before a seizure occurrence. A threshold that is too low can result in false alarms, while a threshold that is too high can cause the ambulatory seizure monitoring system to fail to detect the onset of the seizure state. The appropriate patient threshold can be determined automatically by analyzing previous EEG patient data or input manually through a user interface or via the mobile device 105. A separate device such as a cell phone, tablet, laptop or desktop computer may be used to implement a user interface and may communicate with the mobile device(s) wirelessly or via a wire or optical fiber using well-known interfaces and methods.

In addition, a time interval called the seizure prediction horizon (SPH) and seizure occurrence period (SOP) can be chosen or determined from previous EEG patient data. Time interval is used to define the window of time in which a seizure is predicted to occur following a high PLV signal. When the ambulatory seizure monitoring system crosses into the SPH and SOP time interval, an alert can be sent to a communication device that is notified of a possible impending seizure event (e.g., smartphones, tablets, telephones, etc.) to alert them of the pending seizure event.

In order to avoid spurious detection of locking due to noise and small oscillation coupling, EEG data recorded from different electrode contacts 104 are band pass filtered in order to focus on the frequency areas that produce pre-ictal and ictal behavior. Seizure prediction analysis begins with the decomposition of EEG via Hilbert transformation. The signal can be split into two parts or components, the analytic amplitude (AA) and the analytic phase (AP). Analytic amplitude is the square root of the sum of squares of the real and imaginary parts of the analytic signal. Analytic phase is the arctangent of the ratio of the imaginary part of the analytic signal to the real part of the analytic signal. The decomposed signals are 'unwrapped' by adding multiples of ±2π when absolute jumps between consecutive elements of P are greater than or equal to 2π radians. For an arbitrary continuous time signal v, the Hilbert transform is defined as follows:

$$v'(t) = \frac{1}{\pi} PV \int_{\infty}^{+\infty} \frac{v(t')}{(t-t')} dt' \quad (1)$$

where PV corresponds to the Cauchy Principal Value. A discrete time version of this equation is used for sampled data signals. Using v'(t), the complex analytic signal V(t) is defined as: V(t)=v(t)+i v'(t), where i has the usual meaning of $\sqrt{-1}$. The analytic amplitude (AA) is also given by:

$$A(t)=[v^2(t)+v'^2(t)]^{0.5} \quad (2)$$

and arc tangent of the vector gives the analytic phase:

$$P(t)=\text{atan }[v'(t)/v(t)]. \quad (3)$$

The AA and AP are used to measure the level of amplitude and phase synchrony between EEG signals from paired electrodes using a sliding window of, for example, n=1000, 2500, or 5000 data points. The sliding window acts as a filtering method to sum a larger group of points to calculate PLVs. These synchrony levels, which are termed phase lock value (PLV) and amplitude lock value (ALV), are determined using electrodes in the areas of the scalp where seizure behavior (working electrode) and 'normal' EEG behavior (reference electrode) are found. The PLV can be calculated in the following manner:

$$PLV = \left\| \frac{1}{n} \sum_{t=1}^{n} e^{i[P_1(t)-P_3(t)]} \right\|. \quad (4)$$

$P_1$ and $P_2$ represent the calculated phases (Eq. 3) of the EEG signals from a pair of electrodes at time (t). The value 'n' refers to the window size to sum the PLV. The PLV varies between independent signals and constant phase-lag between the two signals, i.e. EEG signals will either synchronize or operate independently.

In addition, the analytic amplitude can be used to measure the synchrony between two channel's amplitudes or the amplitude lock value (ALV). The ALV is calculated in the following matter:

$$ALV = \left\| \frac{1}{n} \sum_{t=1}^{n} e^{i[A_1(t)-A_2(t)]} \right\|. \quad (5)$$

The ALV measurement can be used in conjunction with the PLV to identify the seizure state, where $A_1$ and $A_2$ are calculated from Eq. 2. The degree of amplitude locking between two channels can determine the similarity between the two amplitudes. If analog circuits are used, sampling can be avoided or performed later in the signal processing chain, and integration would be used in equations (4) or (5), or both, instead of summations, as is well-known in the art.

The PLV and/or ALV can be calculated between the working and reference electrodes. A threshold value of the PLV and ALV is used as a detection marker to indicate seizure occurrence. For example, in one embodiment, the threshold value of the PLV alone is used as a prediction marker. The optimal PLV and ALV thresholds can be determined retrospectively for each patient but may be modified adaptively or tuned in response to historical data recorded for that patient. For an accurate prediction, the prediction marker is set within an appropriate time before a seizure occurrence. The time interval after the prediction marker occurs is set is called the SPH. The seizure occurrence period (SOP) is the time interval of the seizure state, in which the end of the time interval of the SPH is the SOP. Embodiments of the present disclosure employ an SPH+ SOP prediction horizon in which, during interictal periods (i.e., periods far away from any seizure), an alarm should lead to a false prediction.

In accordance with the present disclosure, the seizure event can be found when the PLV and the ALV rise above a patient-based threshold and seizure onset occurs during the SOP. Higher PLV values correspond to channel synchronization. Threshold detection may also be implemented using an analog circuit such as a comparator.

Figure 2B:
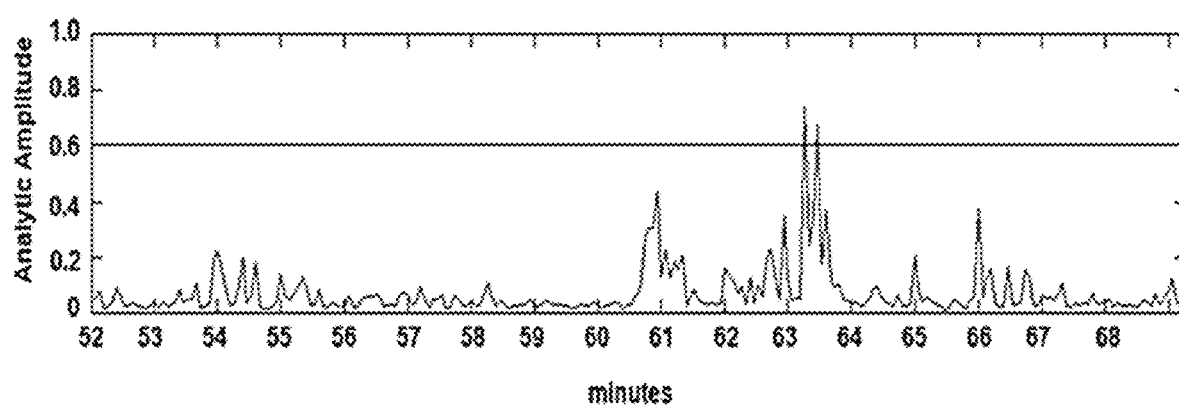
FIG. 2B is a graph illustrating an example of amplitude lock values over a time period for a patient, according to various embodiments of the present disclosure.

Referring back to FIG. 2A, shown is a graph of an example of phase lock values (PLVs) over a time period for a patient. A prediction marker (P) and a seizure event (S) are signified by arrows. Prediction markers and seizure events can be found by the rise of PLVs to or above a patient-based threshold. With regard to FIG. 2B, shown is a graph of an example of an amplitude lock values (ALVs) for a patient with seizures. Seizure events can be found by the rise of ALVs above a patient-based threshold, which also corresponds to the rise of the PLV at S.

Figure 2C:
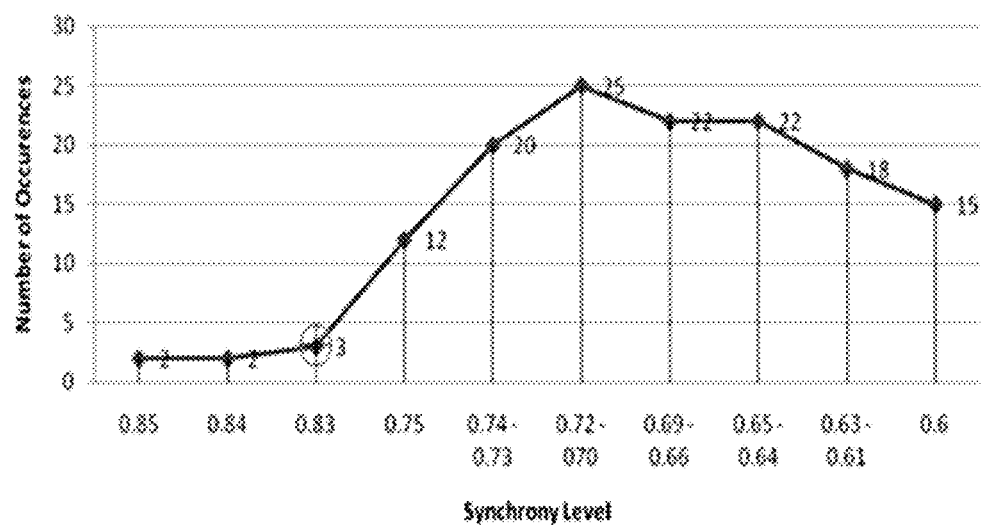
FIG. 2C is a graph illustrating a plot of synchrony levels which are used to establish a threshold marker between normal and seizure activity for a patient's EEG activity according to various embodiments of the present disclosure.

Using specific data examples, FIG. 2C is a plot of synchrony levels of PLV values in one embodiment. It is noted that threshold selection is based on finding the lowest number of Phase Lock Value (PLV) values just before the amount of values rise dramatically. The PLV begins to rise at the synchrony level "0.83" (highlighted by the black cross) which establishes the threshold marker on the PLV display. This figure demonstrates that the smallest number of PLV values at a synchrony level range, i.e., between 0.6 and 0.9 correspond to those values that are higher than the rest of the PLV values that correspond to non-synchronous channel pairs. These higher PLV values correspond to pair-wise channel synchronization. The threshold value "0.83" is selected in order to separate "normal" chaotic neural activity from highly synchronized neural activity found in the seizure state. As the slope of the number of PLV occurrences vs. synchrony level rises sharply from "0.83" and "0.75", we can determine the threshold value between normal and seizure activity for this patient's EEG activity.

Figure 2D:
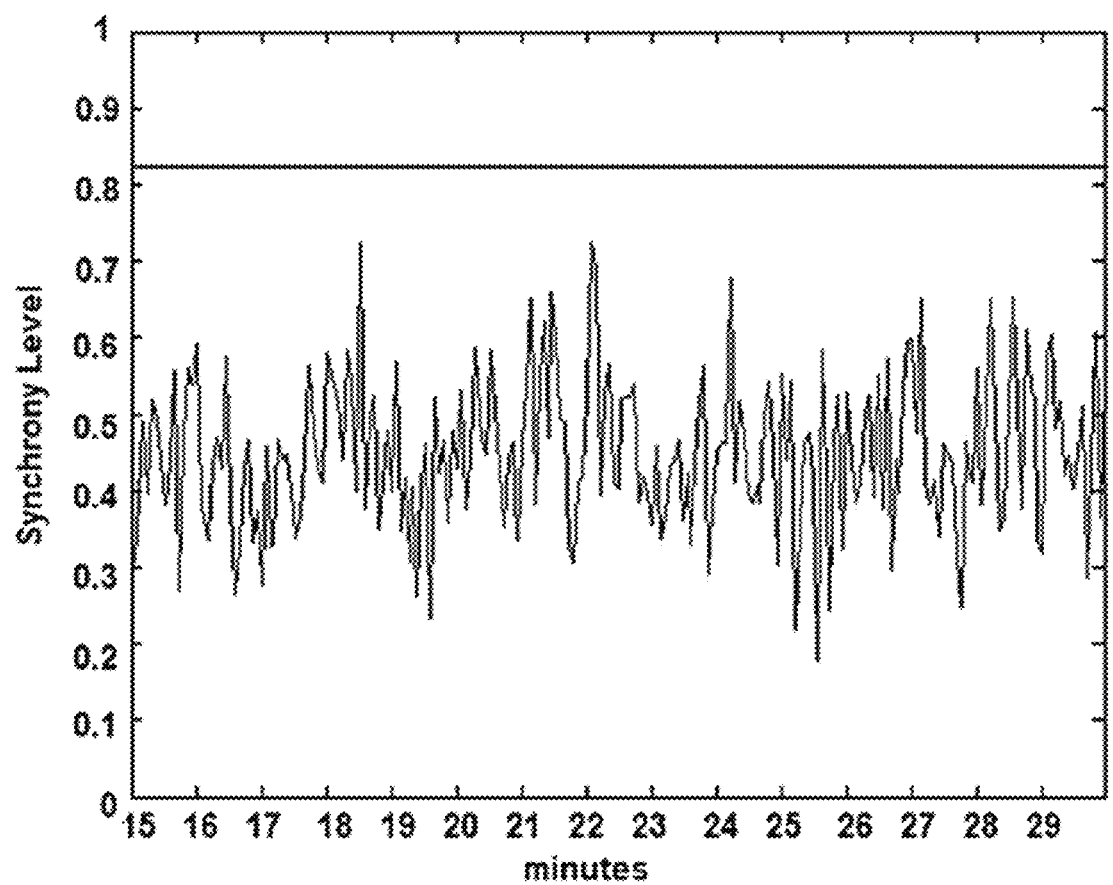
FIG. 2D is a graph illustrating calculated PLV values over an interictal time series according to various embodiments of the present disclosure.
Figure 2E:
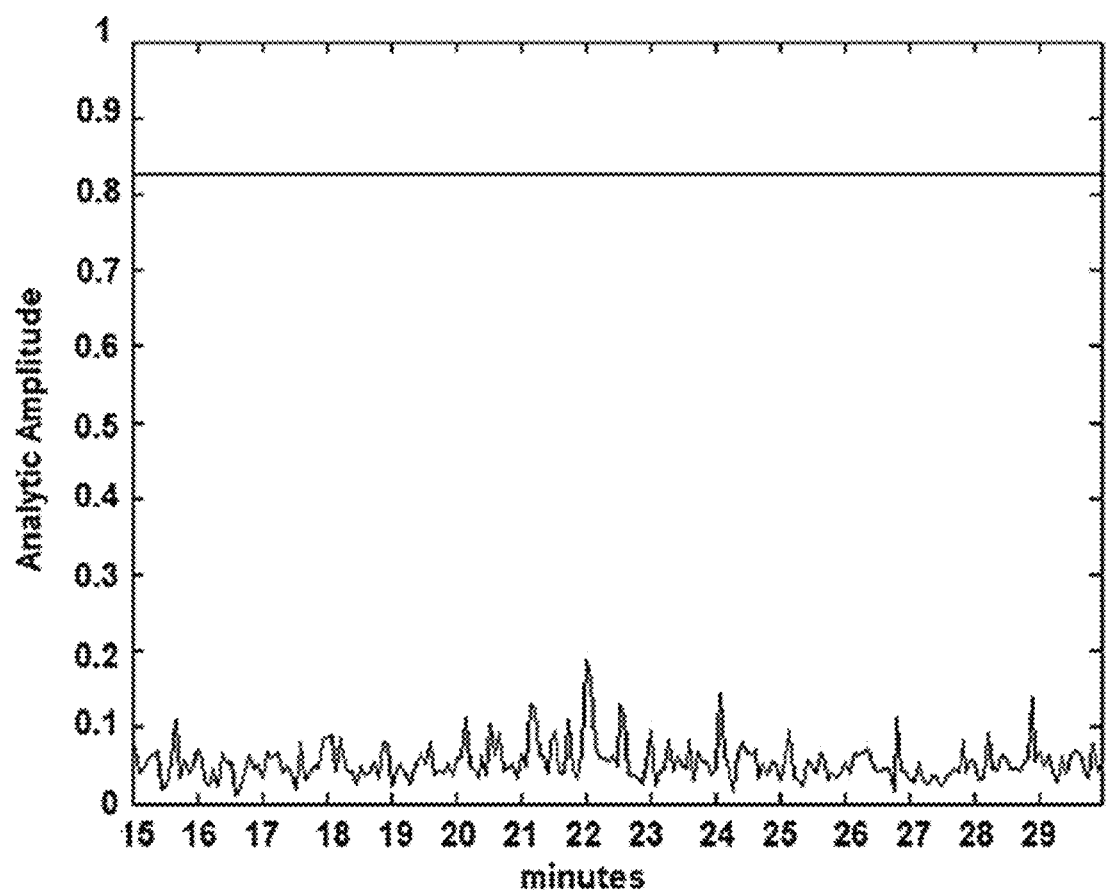
FIG. 2E is a graph illustrating calculated ALV values over an interictal time series according to various embodiments of the present disclosure.

FIG. 2C demonstrates PLV values between 0.6 and 0.85, which corresponds to the calculated PLV values. These higher PLV values correspond to channel synchronization (0.83-0.85). FIGS. 2D and 2E correspond to PLV and ALV values, respectively, over interictal behavior. These values do not reach the patient specific threshold level of "0.83", which demarcates non-seizure behavior from seizure behavior. As discussed, FIGS. 2A and 2B demonstrate the calculated PLV/ALV values over a time series featuring seizure activity. The calculated PLV for this data set shows a pre-ictal marker that rises above a selected threshold in FIG. 2A, which is denoted as "P" for the prediction marker. FIG. 2A also illustrates the PLV rising above a threshold value that corresponds to a seizure event, denoted by the marker "S". FIG. 2B displays the ALV as it signifies the seizure event and demarcates the interictal time period.

As discussed in reference to FIG. 2A, in order to separate basal neurological activity from pre-ictal and ictal behavior, a threshold is set to classify instances of phase locking behavior associated to seizure activity. In accordance with an exemplary embodiment, after calculating the phase component of the signal and calculating the phase locking value for a segment of the time series, significance levels may be derived based on the calculated phases of the compared neural neighborhoods. A synchronization index [0-1] may be applied in order to determine the level of synchronization between oscillating groups, where PLV values approaching one demonstrate a high degree of phase synchronization. The 95th percentile of the distribution of the synchronization indices can serve as significance level. Therefore, a demarcation between lower and higher synchronization indices can determine seizure activity found in the EEG time series.

Phase locking threshold tuning is accomplished on testing one out of three data sets per patient and validation on the last two data sets. Most pre-ictal and ictal behavior of the signal have distinct PLV/ALV values that approach "1" (FIGS. 2A, 2B) vs. interictal or non-seizure behavior (FIGS. 2D, 2E). A threshold is placed between these two states in order to demarcate between these states through analysis of PLV/ALV values on the testing data set and validated through continuous data processing on the next two data sets per patient. Each patient data set will have its own respective seizure vs. non-seizure threshold demarcation. The number of data points used for optimal PLV/ALV calculations, i.e., the value "n" which refers to the window size to sum PLV/ALV values is tested as well and validated throughout the data sets. In order to compensate for cross-patient differences in signal phases and amplitudes, the standard deviation (SD) of a period of non-seizure EEG data for each subject can be measured, i.e., $S_{AAj}$ and $S_{APj}$ for SD of the AA and AP respectively, and used to scale the thresholds for each patient. In one embodiment, amplitude threshold ($SA_{threshold}$) and phase threshold ($SP_{threshold}$) values were chosen experimentally by analyzing and comparing the patterns of changes for different occurrences of seizures and artifacts and selecting the most appropriate value where:

$$S_{AAj} < SA_{threshold}$$

$$S_{APj} < SP_{threshold}$$

Figure 2F:
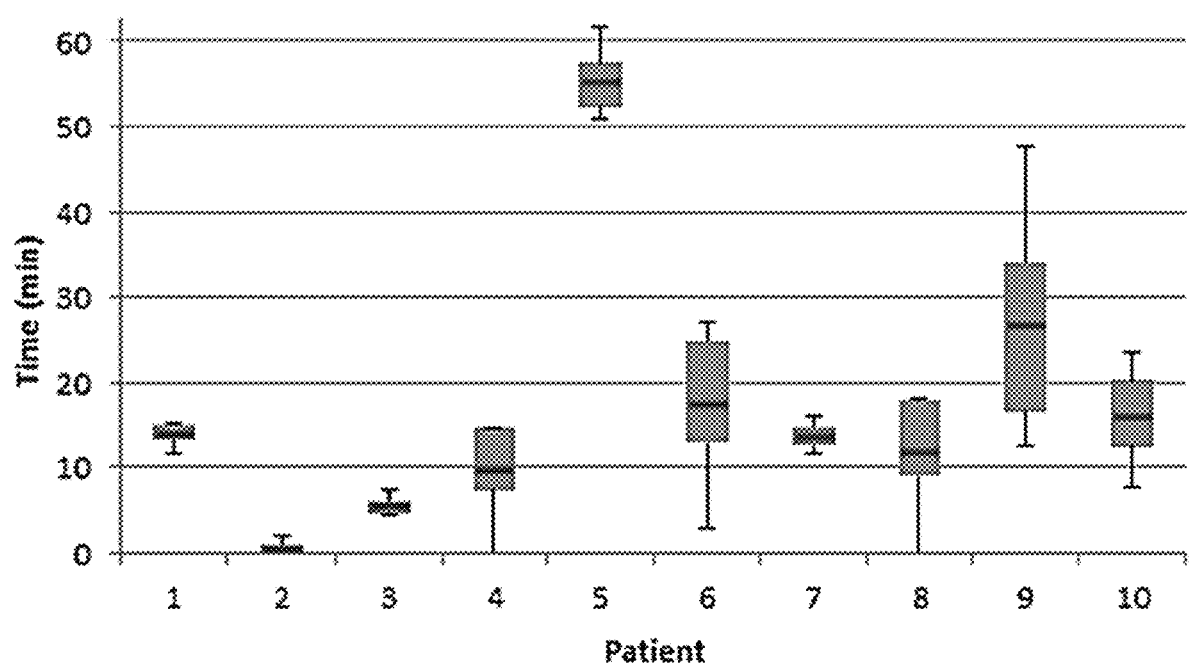
FIG. 2F is a box plot with whiskers displaying a distribution and median of seizure activity for multiple patients according to various embodiments of the present disclosure.

During testing, EEG recordings were collected from ten patients during pre-surgical recording. EEG filtering was accomplished using a Remez filter in brain frequency ranges delta-theta-alpha (1-12 Hz), alpha (6-12 Hz), beta (13-30 Hz), gamma (30-40 Hz), and upper-gamma (40-50 Hz). SPHs ranged from 2 to 62 min, depending on band-pass filtering and patient, where patient "chb06" has the highest SPH among all the rest of the patients. The average SPH+ SOP time period for n=1000, 2500, and 5000 points is 20 min, across all band-pass ranges, as seen in FIG. 2F, in which the figure shows a box plot with whiskers displaying the distribution and median (horizontal bar) of seizure activity for each patient.

In one test of the performance of an exemplary embodiment of the described methodology, true positives are defined as those prediction markers that precede a seizure occurrence within 1 hour, where false negatives are seizures that did not have bookmarked prediction. False positives are then defined as an SPH without the subsequent SOP event or an SOP event that existed outside the 1 hour window. In one test, the described patient-specific seizure prediction and detection methodology for seizure prediction is tested on 10 patients with 30 seizure events and 31 hours of interictal recordings (in the MIT-CHB EEG database). To evaluate an embodiment of the methodology, sensitivity (TP/(TP+FN)), precision (TP/(TP+FP)), the false alarm rate per hour, and the percentage of interictal recordings incorrectly classified as FPs were measured. The false alarm rate per hour and the percentage of interictal data that is incorrectly classified as FPs demonstrate how many false alarms the methodology would generate. Results for all the patients and preprocessing methods are shown in the table of FIG. 2G. Each patient number has the associated MIT-CHB patient number. The gamma band-pass filter produced the highest prediction sensitivity and precision as well as the lowest FP occurrences, with total sensitivity of 77% (classifies 24 preictal events correctly out of 31), a total precision of 88% and 0.17 false positives per hour (three false alarm events in 31 hours of interictal recordings). Due to the low occurrences of FPs, the precision rate produced higher results than the sensitivity rate. The results from the table of FIG. 2G demonstrate that PLV/ALV analysis has a higher rate of detection of seizure vs. random chance detection. PLV/ALV detection can decipher random occurrences of phase locking events thereby detecting true neurological attributes found in seizures events.

Next, exemplary components of an embodiment of the ambulatory seizure monitoring system are discussed. Two main types of EEG sensors or electrodes 104 are currently available in the medical market: active and passive. Passive electrodes are less expensive; however, they require a conductive gel or glue to secure the connection to the area being sensed. Without the glue, accurate brain signals may not be acquired. Additionally, active electrodes were used in some embodiments. The active electrodes can allow brain signals to be read without a glue or adhesive being applied. This makes the electrodes 104 less intrusive to the user. In addition, as one non-limiting example, among others, the set of dry electrodes (e.g., Olimex EEG-AE and EEG-PE) chosen to acquire the EEG signals can be inexpensive and/or open source. The electrodes can be adapted to receive EEG signals from a patient.

The brain comprises billions of neurons that send electrical charges from one to another, creating electrical potential oscillations that can be measured using a voltmeter. Because these voltages are very small, an amplifier device 113 can be used to bring the amplitude of the brain signals up to a level that can be measured and interpreted. Therefore, the defining objective for an EEG specific amplifier 113 benefits from a combination of high gain and low noise operation. In this pursuit, the solutions below were considered. An amplifier (e.g., an open source Olimex-SMT) was chosen to amplify the EEG signals acquired from the electrodes (e.g., Olimex EEG-AE & EEG-PE). In one non-limiting example, among others, a 2-channel USB EEG amplifier (e.g., Olimex EEG-AE & EEG-PE) was used because it has the associated analog and digital functionality on one chip.

In this non-limiting example, among others, a simple Bluetooth module 120 (e.g., a HC-06 based module by Atomic Market) is chosen to transmit the amplified EEG signals. The Bluetooth module is configured to be a slave device that transmits the serial data from the amplifier 113. The Bluetooth module 120 is reconfigured so that the baud rate matched that of the amplifier 113.

The user's mobile device 105 may be an important component in the system, in one or more embodiments. In one embodiment, the mobile device 105 sets up and maintains all of the Bluetooth connectivity, processes the data, controls the patient and health provider settings, and invokes the notification system. While an Android Operating System (Android OS) was chosen for its familiarity (Java) and open platform architecture, other operating systems can be used such as the Apple iOS and iPhone, Microsoft Windows using a Windows-based phone or tablet, Linux (such as an Ubuntu-based phone or tablet), or a tablet or other device containing a processor. The overall architecture of the application includes searching, pairing, and connecting to the Bluetooth module 120; receiving data via Bluetooth; processing the data using the seizure prediction algorithm; configuring the notification and patients settings; and sending notifications. The Android OS has built-in interfaces to an RFCOMM class that assist with Bluetooth connections. While the Android OS handles the searching and pairing, the connection can be maintained completely by an application program 108 of the mobile device 105. The mobile device 105 can implement a Bluetooth service that spawns a thread to handle setting up the connection in the background, along with another thread to handle the incoming data. The data can be passed to another class via a Handler which maintains a buffer and processes the data in chunks. When a seizure prediction biomarker occurs, a broadcast can be sent to the notification system which handles all of the notifications that were set up by the patient in the GUI application. In the exemplary configuration described herein, all of the settings configured by the patient and the health provider can be stored as private elements in Android's 'SharedPreferences' database. This was chosen because the variables can be accessed from any part of the application program 108 of the mobile device 105, but can only be called from within the application program 108 that created them. This ensures security and also allows the application to be extended for other purposes.

In some embodiments, among others, portability and rechargeability are the primary concerns regarding the system's power supply. Considering this, in one implementation, the 5 VDC-1A, myCharge Amp 4000 lithium polymer battery was chosen to support the system. The myCharge Amp interfaces with the system using a USB connection.

In one embodiment, among others, the architecture of the ambulatory seizure monitoring system enables the most efficient use of power usage and component flexibility throughout the system. An Arduino board can be used to digitize the EEG signal, interface to an amplifier 113 which would provide a high gain and low noise operation on the signal, and provide an interface with a Bluetooth module 120 to transmit the data. The bulk of data processing can be performed on the Android device 105, where an application resides and can utilize the current power source of the mobile device 105. Therefore, the power consumption can be minimized on the conditioning of the EEG signal, and data processing can be managed as an application on an OS environment. Through this architectural configuration, it is easy to update the software through application downloads, and provide the capability for the mobile device 105 (e.g., a smartphone or tablet) to receive EEG data from a Bluetooth enabled EEG data acquisition device 106. In this non-limiting example, among others, there are four major components to the system, including: acquisition, processing, transmission, and notification.

In addition, as one skilled in the art can appreciate, the individual components of the various embodiments can be designed in one or more integrated circuit components. As one non-limiting example, among others, the functionality associated with various individual components can be embodied in dedicated hardware, a combination of software/general purpose hardware, or a combination of software/general purpose hardware and dedicated hardware. If embodied in dedicated hardware, each can be implemented as a circuit or state machine that employs any one of or a combination of a number of technologies. These technologies may include, but are not limited to, discrete logic circuits having logic gates for implementing various logic functions upon an application of one or more data signals, application specific integrated circuits (ASICs) having appropriate logic gates, field-programmable gate arrays (FPGAs), or other components, etc. Such technologies are generally well known by those skilled in the art and, consequently, are not described in detail herein.

In one embodiment of the EEG data acquisition system 106, among others, four dry, active electrodes 104 are used to detect the EEG signals. These small sensors are placed in various locations on the patient's head. A dry, passive electrode is placed on the patient's ear to serve as a reference. For convenience and a reliable connection, the electrodes 104 are held by a headband or cap, in one embodiment.

Figure 3:
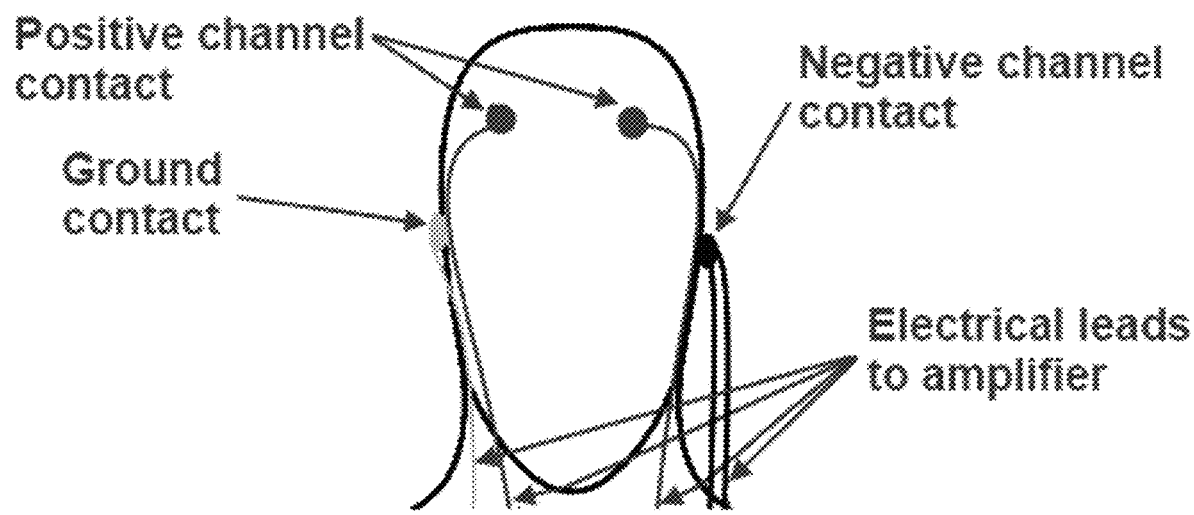
FIG. 3 is a drawing of an example of an electrode configuration on a head of an individual, according to various embodiments of the present disclosure.

With reference to FIG. 3, shown is an example of the electrode configuration on an individual's head. Positive channels can provide EEG data acquisition. Ground and negative (reference) channels can be connected to earlobes. In the illustrated embodiment, the electrodes 104 lead to an amplifier 113 for signals to be transmitted via the Bluetooth module 120 to a mobile device 105 for data processing. Accordingly, the EEG signals can be fed into a 2-channel amplifier 113 (e.g., an Olimex-SMT). The amplifier 113 can be designed specifically to process EEG signals. FIG. 4 is a table that illustrates the various electrode settings.

In a non-limiting example, among others, the data are transmitted from the amplifier 113 (e.g., Olimex-SMT) to the mobile device 105 for processing. To transmit the data via a Bluetooth module 120, RFCOMM sockets can be established between the two devices. The Serial Port Profile (SPP) of the Bluetooth module 120 can be used to transmit USB serial data from the amplifier 113 (e.g., an Olimex-SMT board) to the mobile device 105 via the data pins. This establishes the mobile device 105 as the master and the Bluetooth module 120 as the slave. Therefore, an application program 108 on the mobile device 105 handles the searching, pairing, and connecting to the Bluetooth module 120, and the module 120 acts as a server that transmitted the data from its data pins over the sockets, in some embodiments.

The application program 108 can verify that the Bluetooth is ready, and then it can spawn, e.g., an Android Activity to handle the searching and selecting via a device list. If the radio link module device 120 (e.g., Bluetooth module) has not been seen before by the mobile device 105, the user can be prompted to input a PIN code and select a desired device. For example, in one embodiment, once a Bluetooth module 120 has been selected from the list, the MAC address can be passed to a Bluetooth service to handle the pairing and connection.

The Bluetooth service can run in the background and handle all of the pairing and connection tasks to set up the RFCOMM sockets. Once the sockets are established, the service can use an SPP profile to listen for and receive the data from the RFCOMM socket. The bytes received can then be parsed and stored into buffers for later processing. In one embodiment, at least two buffers or a ring buffer or ring of buffers are used. Once enough data have been collected, the buffers can then be passed to a Java class that handles processing the data using a seizure prediction algorithm.

In one embodiment, among others, as data are sent via Bluetooth and received by the mobile device 105, they are placed in a buffer for processing. Once the buffer reaches a specific number of elements, a thread can be spawned and the buffer is passed to the thread for processing. Once processing is complete, the buffer can be flushed to allow new data to be acquired. Data structures were developed to help aid in the processing, including support for data sets that include complex numbers, filtering functions, and multidimensional array operations. Based on the seizure prediction algorithm, the final output can be transformed into a binary output using a threshold that is set to a specific value by the health care provider. The threshold value can be established or defined for each patient through an external algorithm. The value 'GlobalMax' can be utilized to normalize the processed EEG to be between [0, 1]. This value is patient specific. Once a seizure prediction biomarker is detected, the application program 108 can construct and commit the relevant notifications. The notification types and destinations can all be configured by the user through the main user interface of the application program 108. The user can choose to send notifications via voice, audio, email, SMS, telephone calls, or use Android's (or other OS) notification system (i.e. pop-ups, notification bar, sounds, voice, audio, etc.).

Once a seizure prediction marker is detected, in one embodiment, the application program 108 progresses through several conditional statements to determine how to send notifications. The user can select the type of notifications to use by activating or deactivating the radio buttons, which change flags in the background that affect the results of said conditional statements. The user can also personalize the notification recipients by using the appropriate buttons that are in the respective lists labeled "SMS settings," "Email settings," or "Call settings." The "Add" button can generate a pop-up window to allow the user to manually type in a contact or go to the phone's contacts to populate the lists. The user may remove recipients by using the appropriate delete ("Del") buttons for each contact in their respective list. Once the settings are final and the connection to the EEG acquisition system 106 is initiated, the application program 108 can send the notifications based on these settings, i.e. "Patient ID, Date, and Time."

Figure 5:
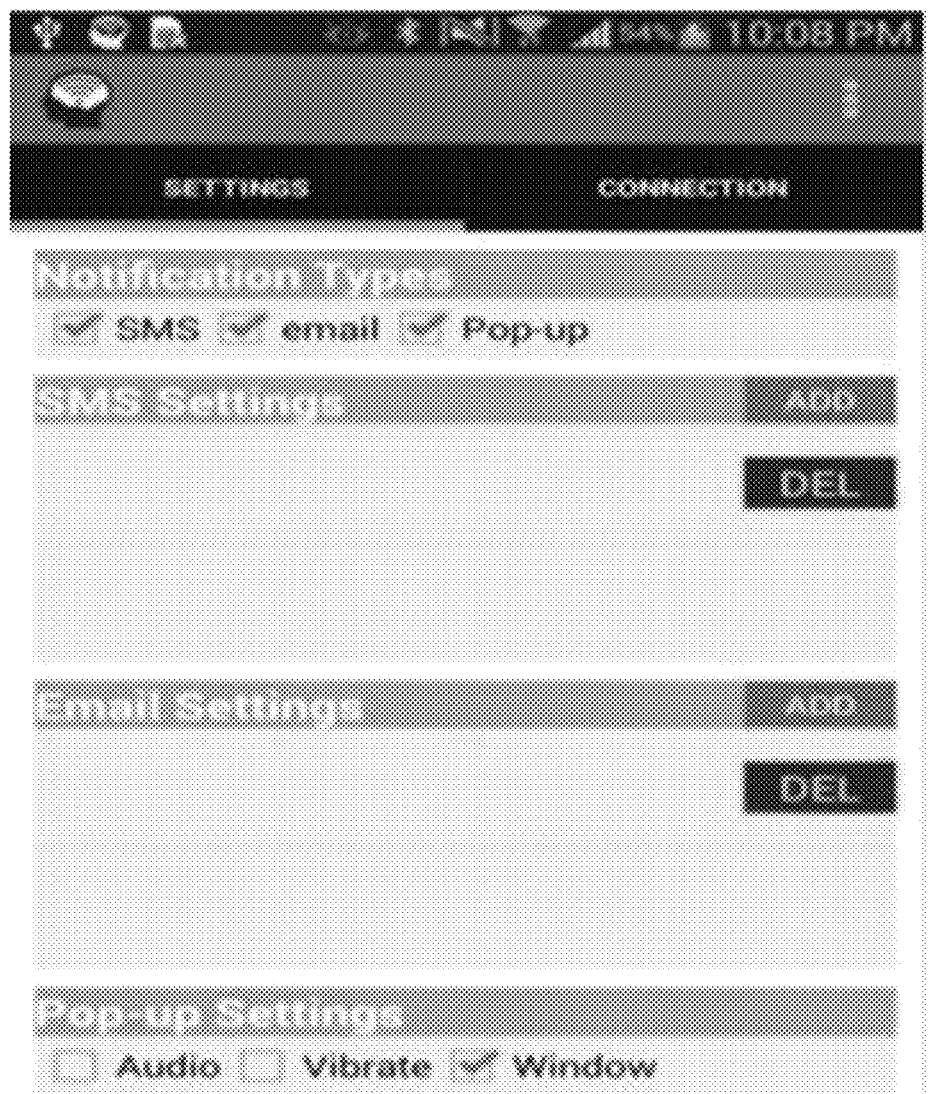
FIG. 5 is an example user interface illustrating various configurable notification settings, according to various embodiments of the present disclosure.

With reference to FIG. 5, shown is an example of a user interface (or GUI) illustrating various configurable notification settings. The notification settings are configurable using a graphical user interface of the application program 108. Upon successful detection of a seizure prediction biomarker, the notification settings can determine how a notification is sent, for example, via SMS, email, or an Android popup notification.

Figure 6:
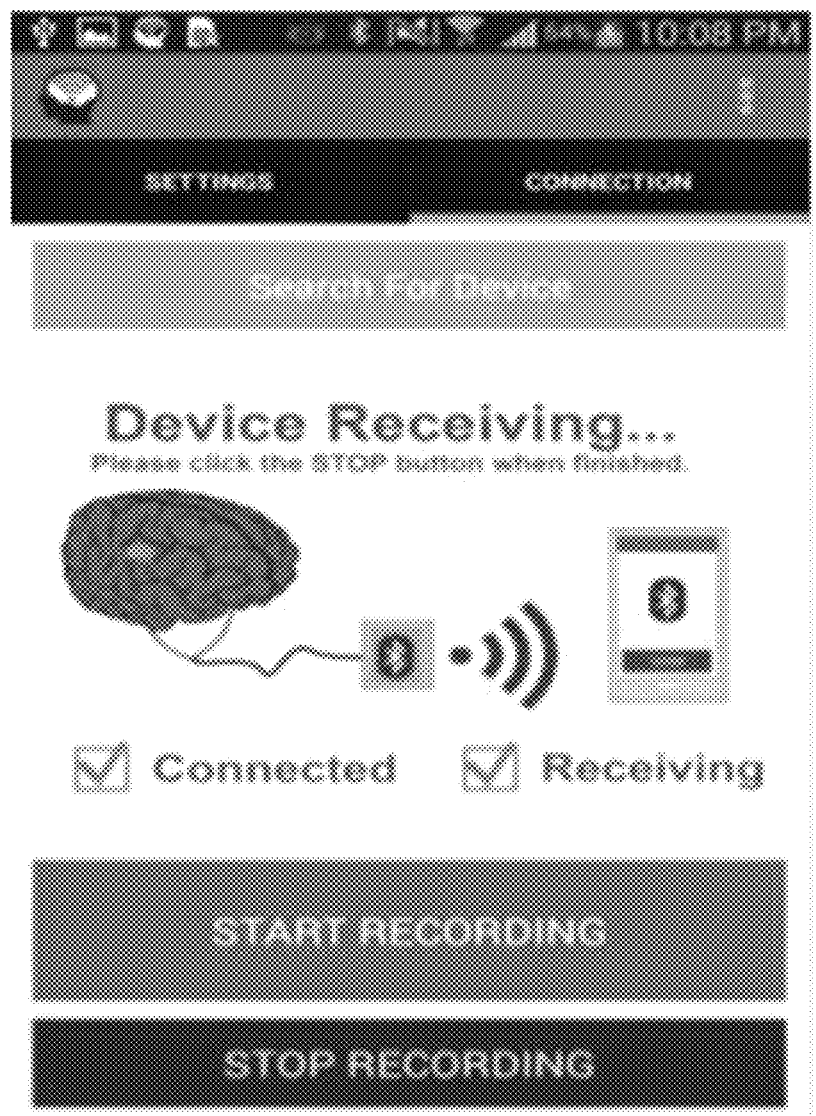
FIG. 6 is an example user interface for establishing data transfer pairs, according to various embodiments of the present disclosure.

With reference to FIG. 6, shown is an example of a user interface (or GUI) establishing data transfer pairs. In this embodiment, among others, a data pairing can be between the amplifier 113 and a mobile device 105. For example, the amplifier 113 sends EEG data via a Bluetooth module 120 to a mobile device (e.g., smartphone) 105. The Bluetooth module 120 can search for an available smartphone or other mobile device to process data.

Using the test data set, the data are processed on the mobile device 105 and the results were passed to a notification component of the application program 108. When a seizure prediction biomarker was encountered, the notification component responded with the appropriate notifications based on the user specified settings (i.e. SMS, email, popup, telephone call, etc.).

To verify the functionality of an exemplary embodiment of the complete ambulatory seizure monitoring system, the amplifier 113 and Bluetooth module 120 were initially powered by a battery during testing. Also, the mobile device 105 was paired with the Bluetooth module 120. After the electrodes 104 were appropriately placed on a subject, channel 1 and channel 2 graphs were updated in real time from the EEG signals. A test was conducted in order to confirm the appropriate signals were being acquired from the electrodes 104 and the amplifier 113. Data acquisition is performed via the EEG data acquisition component 106 (e.g., using an EEG SMT Board) which gathered EEG data from the active electrodes 104. Wireless communication was implemented using Bluetooth with a baud rate set to 57600, which transmits data sampled at 256 Hz.

Figure 7:
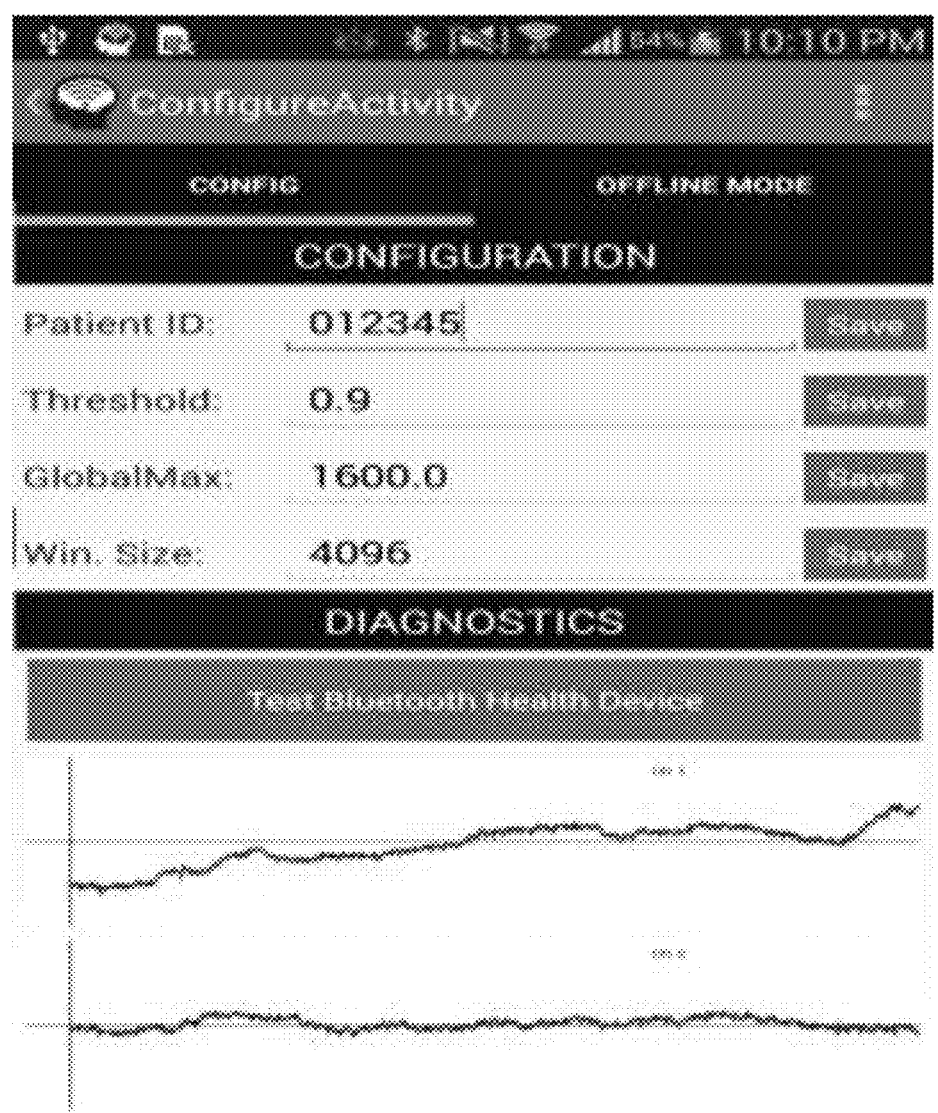
FIG. 7 is an example user interface for configuring patient thresholds for an individual patient, according to various embodiments of the present disclosure.

With reference to FIG. 7, shown is a user interface (or GUI) used to configure or tune the setting for a patient. "Patient ID" identifies the specific transmitted data stream. The value "Threshold" separates seizure states from non-seizure states by setting a target for processed EEG data that rises above a patient specific value, from [0, 1]. 'GlobalMax' normalizes processed data from '0' to '1' based on the data segment (Window Size), so that seizure states can be processed and detected.

The power consumption of the system was analyzed in two parts: the power consumption of the external battery as well as the effect of the application program 108 and related components (e.g., seizure feature extraction module 111) on the battery of the mobile device 105. To calculate the power consumed by the electrodes 104, amplifier 113, and radio link module 120 on the external battery, the voltage from the battery was measured using a voltmeter and the current from the battery to the components. In order to calculate the maximum power consumption, the measurements were taken when the system was acquiring and transmitting data. It is difficult to quantitatively analyze the effect of the relevant applications on the battery of the mobile device 105. However, a general idea was gained by contrasting the battery life when the applications (e.g., application program 108, seizure feature extraction module 111, etc.) were running in comparison to when they were not running. In addition, there are several diagnostic applications that estimate the power drain caused by a particular application, for example "Battery Stats Plus." This information was also considered. The output voltage was measured to be V=5.049V with I=99.077 mA. Therefore, P=IV=(5.049V) (99.077 mA)=500.24 mW.

The system lifetime was evaluated by monitoring how long the ambulatory seizure monitoring system could continuously acquire, transmit, and process the EEG data. Data are collected and transmitted to the mobile device 105 to be processed. The lifetime of the system was observed to be 12 hours, where all components of the system were operating under maximum load. Also, the system is capable of acquiring and processing real time data with less than a second delay.

Offline testing is conducted using an EEG data set. The data are loaded into the application program 108, processed, and then the notifications were sent. The system is capable of acquiring and processing real time data with less than a second delay. The lifetime of the system was observed to be 12 hours, where all components of the ambulatory seizure monitoring system were operating under maximum load.

Figure 8:
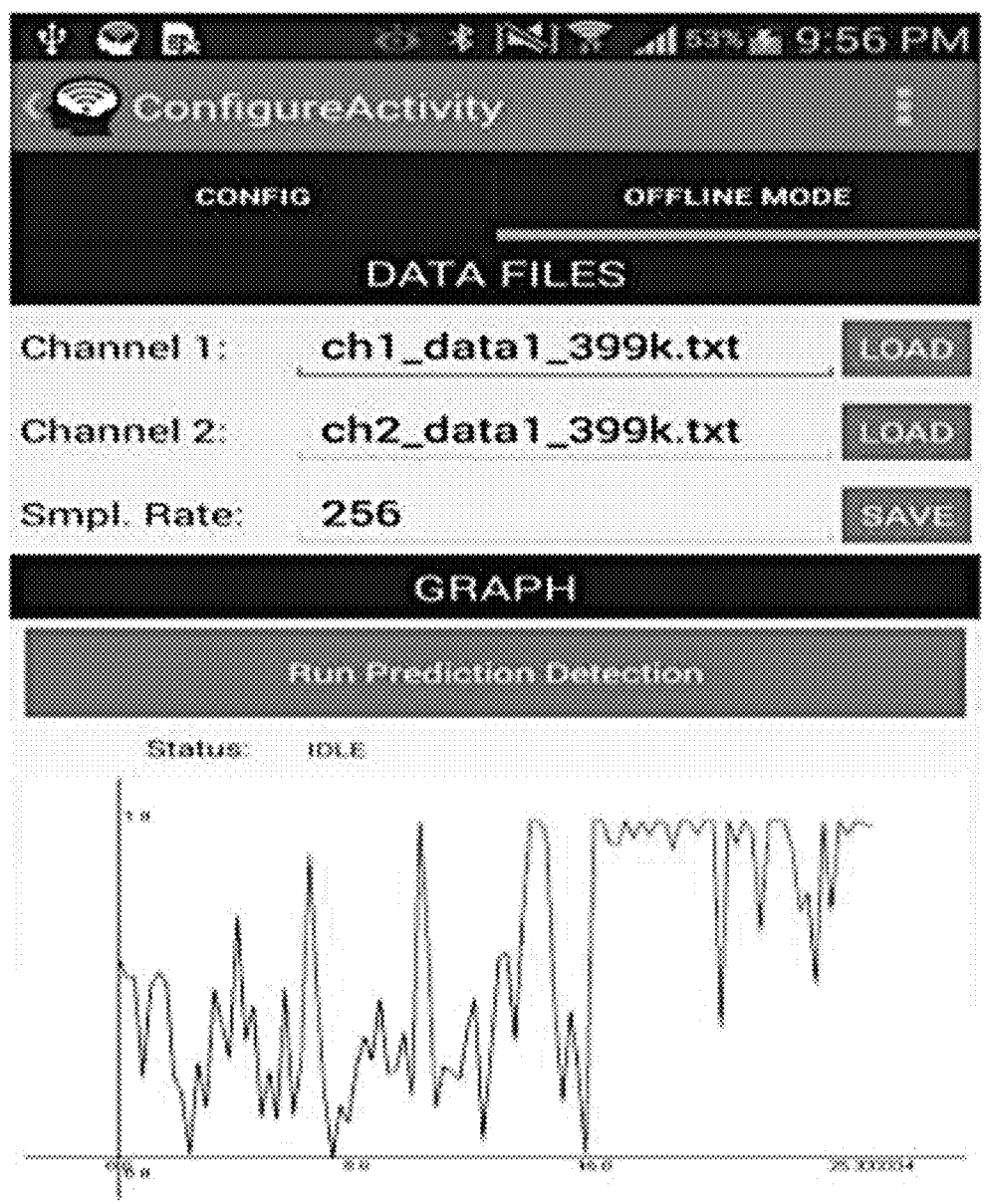
FIG. 8 is an example user interface for an offline mode that enables testing of previously recorded data, according to various embodiments of the present disclosure.
Figure 11:
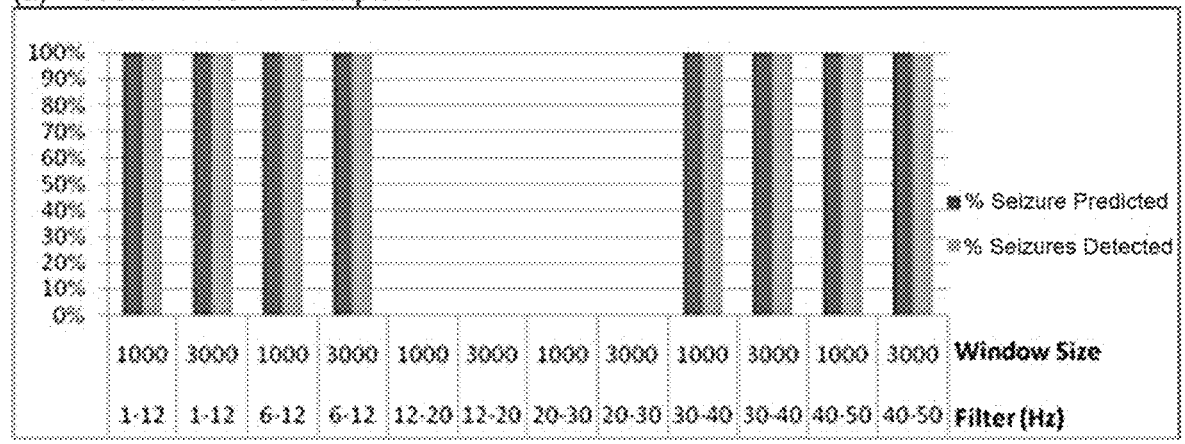
FIGS. 11A-F are graphs illustrating examples of seizure prediction and detection sensitivity in various patients, according to various embodiments of the present disclosure.
Figure 11:
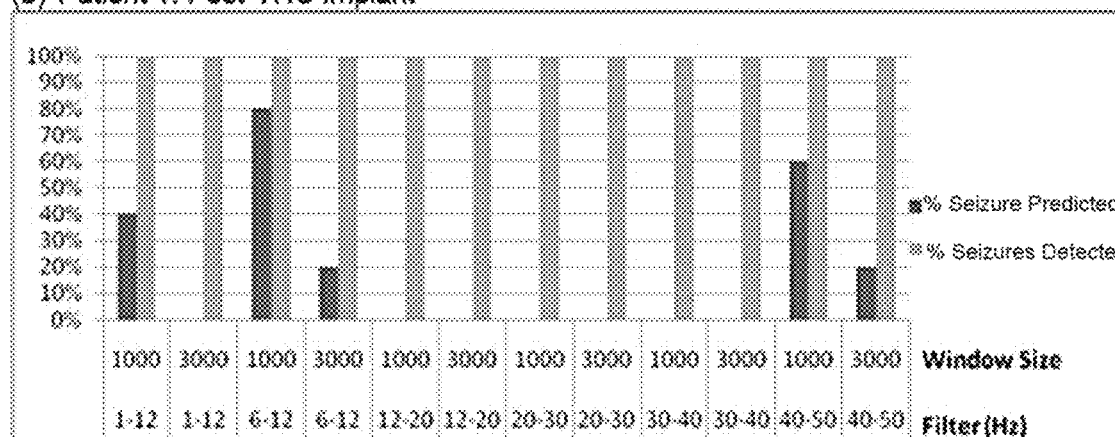
Figure 11:
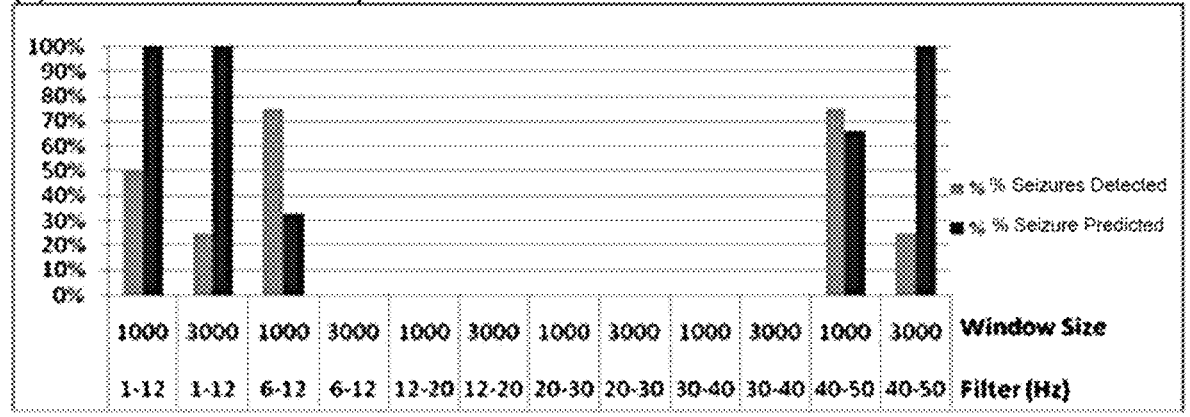
Figure 11:
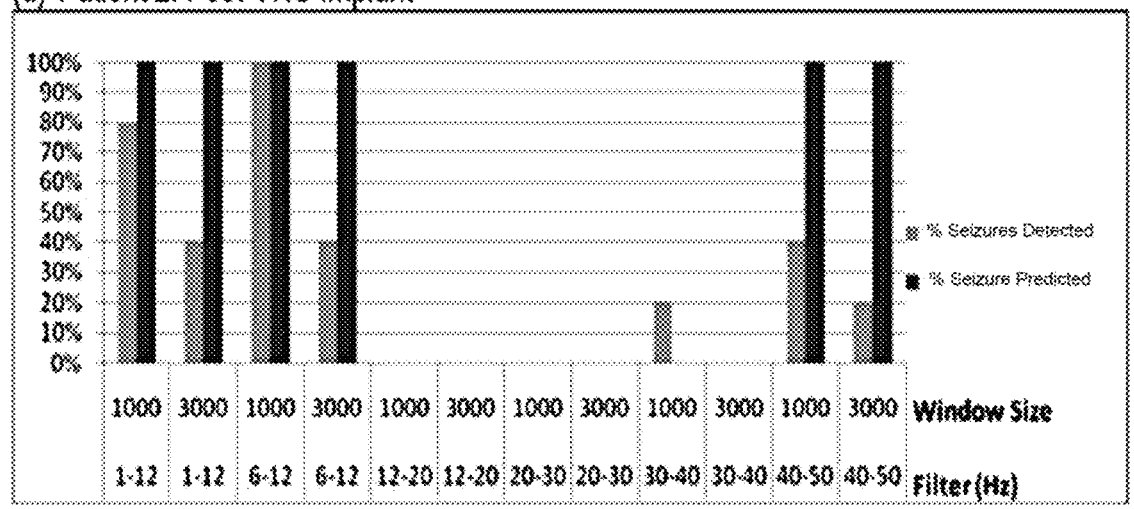
Figure 11:
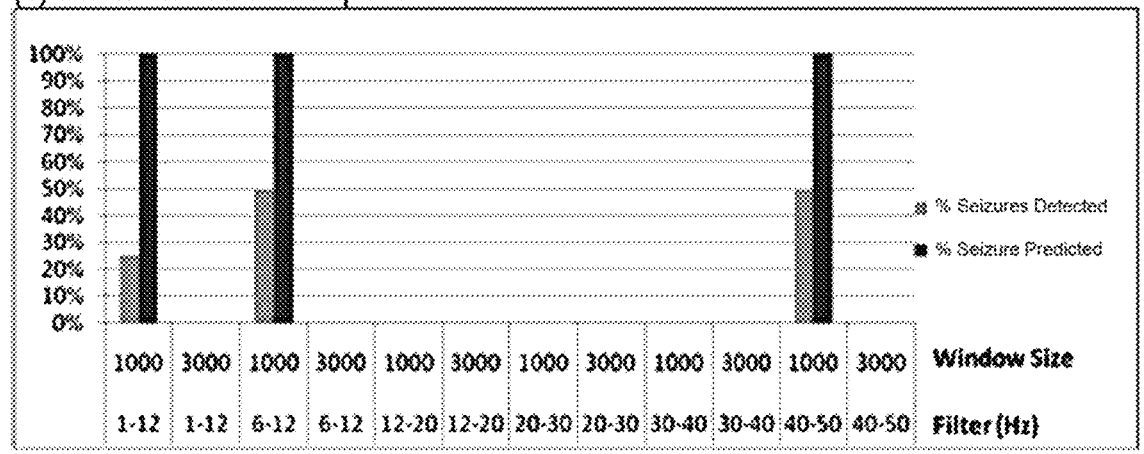
Figure 11:
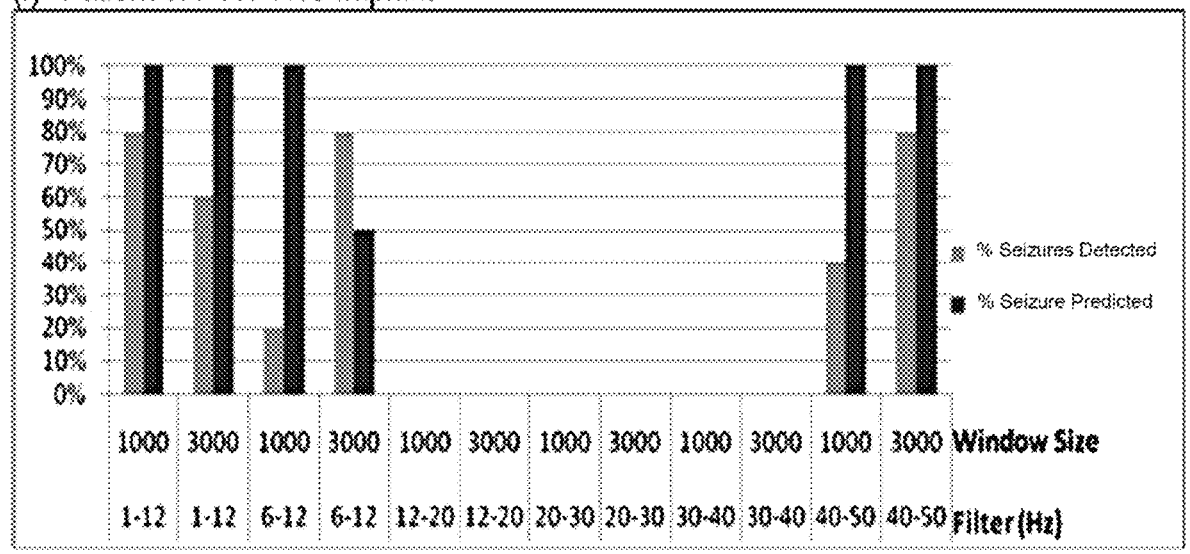

Turning to FIG. 8, shown is a user interface (or GUI) of the application program 108 for an Offline Mode that enables testing of previously recorded data. Specifically, the Offline Mode enables device testing based on previously recording EEG seizure data. This screen can be used for testing additional EEG data acquisition systems, where the sampling rate of the collected data is entered in the acquisition system. The 'Run Prediction Detection' display features processed EEG seizure data, where lines colored in red demonstrate pre-seizure states (predicted) and post seizure states (detected). Seizure detection utilizes the seizure prediction and detection algorithm described previously and will perform as shown in FIG. 8.

A scenario where the seizure monitoring system may be considered involves patients with intractable types of seizures who are candidates for vagus nerve stimulator (VNS) implants. A physician would want to monitor the patient prior to surgery in order to gather frequency and intensity of the seizure state. Additionally, seizure monitoring involves gathering attributes of the neural signals, such as band-pass frequency selection and window size for data processing of incoming signal.

EEG data were used to test exemplary systems/methods of the present disclosure using patients with medically intractable epilepsy, who were candidates for the vagus nerve stimulator (VNS) surgical treatment. Features of normal/abnormal brain activity were monitored for 60-90 minutes. Action potentials were captured at a sampling rate of 250 points/second. Testing of the Seizure Monitoring algorithm features EEG recordings which were collected from three patients during pre- and post-VNS implant recording. The length of ictal behavior ranged from 8-12 seconds.

FIG. 9 and FIG. 10 display the number of seizures per patient, seizures detected, and seizures predicted by an exemplary system/method of the present disclosure. EEG filtering is accomplished using a Remez filter in brain frequency ranges delta-theta-alpha (1-12 Hz), alpha (6-12 Hz), beta (13-30 Hz), gamma (30-40 Hz), and upper-gamma (40-50 Hz).

Specifically, FIG. 9 displays a table of a number of seizures detected pre- and post-implant per frequency band filter range and window size. FIG. 10 displays a table of a number of seizures predicted pre- and post-implant per frequency band filter range and window size. The experimental findings illustrate that there can be a triggering mechanism through the PLV method that enables seizure prediction and can enable better control of an implanted seizure control system through seizure prediction. In this manner, a pulse generator could be programmed to deliver electrical stimulation during the SPH time interval to the brain if the PLV value rises above a threshold range.

FIGS. 11A-F show graphs that illustrate seizure prediction and detection sensitivity using the PLV methodology in accordance with embodiments of the present disclosure. Sensitivity calculations were processed per patient, where sensitivity calculations use the total number of pre- and post-implant seizures per patient that were identified by the clinician who provided the EEG data set for this research. This value is used to calculate the number of true positives.

The highest seizure detection sensitivity for patient 1, 2 and 3 was from 100%, 75%, and 80%, respectively depending on frequency band selection. The highest seizure prediction sensitivity for Patient 1, 2 and 3 was 80%, 100%, and 100%, respectively. The bandwidth 6-12 Hz (alpha) has the most occurrences of seizure prediction and detection markers across all the pre and post implant EEG recordings.

The ambulatory seizure monitoring system architecture and related methods facilitate an EEG monitoring capability that provides a better understanding of the patient's seizure condition, and enables an enhanced approach to patient monitoring. Ultimately, the patient will be provided the best intervention based on the analysis of an exemplary embodiment of the ambulatory seizure monitoring system.

According to the Centers of Disease Control and Prevention, roughly 2.3 million adults and 467,711 children in the United States have epilepsy. Nearly 150,000 Americans develop the condition every year. People with epilepsy live in constant fear of an impending seizure. For extreme cases, they are unable to drive or do many of the daily functions most people take for granted and therefore are limited in the daily activities. When a patient with epilepsy has a seizure, he or she may stay in a hospital bed while EEG (electroencephalography) tests are being done in an attempt to diagnose the cause and severity of the seizures. An exemplary BCI system or device of the ambulatory seizure monitoring system addresses the need for long-term monitoring of the patient's seizure condition in order to provide the clinician a better understanding of the seizure's duration and frequency, and ultimately provide the best remedy for the patient. Experiments were conducted in accordance to the University of Memphis IRB regulations, IRB reference protocol: E06-80.

Accordingly, embodiments of the present disclosure provide a robust seizure prediction methodology enabling a "closed-loop" system that only activates as impending seizure activity is detected. Such a system can eliminate ongoing stimulation to the brain, thereby eliminating such side effects as coughing, hoarseness, voice alteration, and paresthesia, while preserving overall battery life of the system. As discussed, embodiments of the present disclosure use Phase/Amplitude Lock Values (PLV/ALV) which calculate the difference of phase and amplitude between electroencephalogram (EEG) electrodes local and remote to the epileptic event. PLV is used as the seizure prediction marker and signifies the emergence of abnormal neuronal activations through local neuron populations. In various embodiments, PLV/ALVs are used as seizure detection markers to demarcate the seizure event, or when the local seizure event has propagated throughout the brain turning into a grand-mal event.

Exemplary embodiments of the seizure prediction and detection methodology of the present disclosure have been tested on interictal and ictal events against a commonly available large data set (e.g., MIT-CHB EEG database), exhibiting a high degree of sensitivity and precision. It was observed through human EEG testing that the signal captured through high-density electrodes exhibited the following traits: pre-ictal PLV values reach a threshold several minutes before the seizure event. This state may represent the initial imbalance of the electrical activity of the brain through seizure neuron firing. The phase of signal emanated from these neurons will be much longer than normal neuron firings. The SPH is defined as the SPH+SOP where the SPH initiates the seizure activity, followed by a reconstitution state where the brain attempts to restore the electrical activity in the presence of initial abnormal neuron firings. This effect is shown as PLV and ALV values return to below threshold values, and the PLV/ALV values once again rise to the threshold value signaling the seizure event and the last part of the SPH+SOP period. In this manner, the electrical activity of the brain is overcome by the abnormal neuron signals, and will eventually fall into an imbalanced state. This event is represented by the SOP part of the seizure activity. Through early seizure detection, this methodology can be implemented into a seizure control system that can aid in the management of recurrent seizure activity.

Accordingly, embodiments of the present disclosure improve upon seizure detection techniques that are known in the field, as demonstrated below.

For example, U.S. Pat. No. 5,311,876 describes a system that looks at the trend of EEG activity through logistic regression, whereas an exemplary embodiment of the ambulatory seizure monitoring system is capable of looking at the quick changes in the signal at a given window's instance, in which a non-overlapping sliding window may be used to calculate the phase and amplitude lock values between working and reference electrodes on the scalp. Further, an embodiment of the ambulatory seizure monitoring system uses non-linear band-pass filtering and Hilbert transformations signal decomposition which has the capability to find the rapid changes in the EEG signal in order to locate extremely brief seizure activity, in some cases lasting only 6-12 seconds.

U.S. Pat. No. 5,857,978 focuses on filtering techniques versus feature extraction to find seizure activity. Whereas, embodiments of the ambulatory seizure monitoring system has patient-based parameter tuning for optimal seizure prediction and detection, such as patient-based seizure thresholds for prediction horizon and seizure occurrence states. As part of the patient tuning aspect of one exemplary methodology of the present disclosure, a seizure threshold is calculated, which demarcates non-seizure behavior from seizure behavior U.S. Pat. No. 5,995,868 describes the application of an estimate of power spectral density (PSD) on a waveform of an individual's brain activity during a seizure. The resulting PSD's are compared with PSD's obtained from interictal segments. Power-frequency envelopes are then computed, more heavily weighing the spectra at frequencies which yielded the greatest separation between the ictal and interictal PSD values. After filtering, most recent values are divided by the less recent values to provide an 'ictal' or seizure index. Seizure detection is provided when the index reaches a given threshold. On the other hand, an exemplary embodiment of an ambulatory seizure monitoring system of the present disclosure provides a complete system featuring band-pass filtering and patient-based feature selection parameterization. For example, due to the implementation of the Hilbert transform, very fast changes in the waveform not only detect short bursts of pre-ictal activity, it would be able to detect short-term to gran-mal seizure activity found in pediatric cohorts.

U.S. Pat. No. 6,304,775 features a nonlinear dimensionality approach to seizure detection in measuring the amount of 'Chaoticity' in the EEG time series. This algorithm has a 5-minute sliding window which enables the detection of pre-ictal activity, i.e. activity leading up to the seizure event versus seizure prediction. The Lyapunov exponent calculation used in this study is measured across all electrodes, providing a value corresponding to differing degrees of chaoticity to semi-periodic behavior, which is a signature of seizure activity. In comparison, an exemplary embodiment of the ambulatory seizure monitoring system can utilize a sliding window adjusted to 6-20 seconds, for example, thereby finding rapid signal changes that can provide quick interictal bursts signifying seizure prediction markers. Additionally, non-linear dynamic measurements that try to quantify the divergence, convergence or limit cycles of complex systems such as the brain generally need a large number of data sets in order to quantify the behavior of the system. However, embodiments of the ambulatory seizure monitoring system use signal processing techniques which have been found to quantify very quick changes in the state of the system into a series of epochs that can be correlated to causal events, such as interictal and ictal events.

Additional features and advantages of embodiments of the present disclosure are also discussed in a paper by the inventors, titled "Seizure Prediction and Detection Via Phase and Amplitude Lock Values," *Frontiers in Human Neuroscience*, published Mar. 8, 2016, which is incorporated herein by reference in its entirety.

Figure 12:
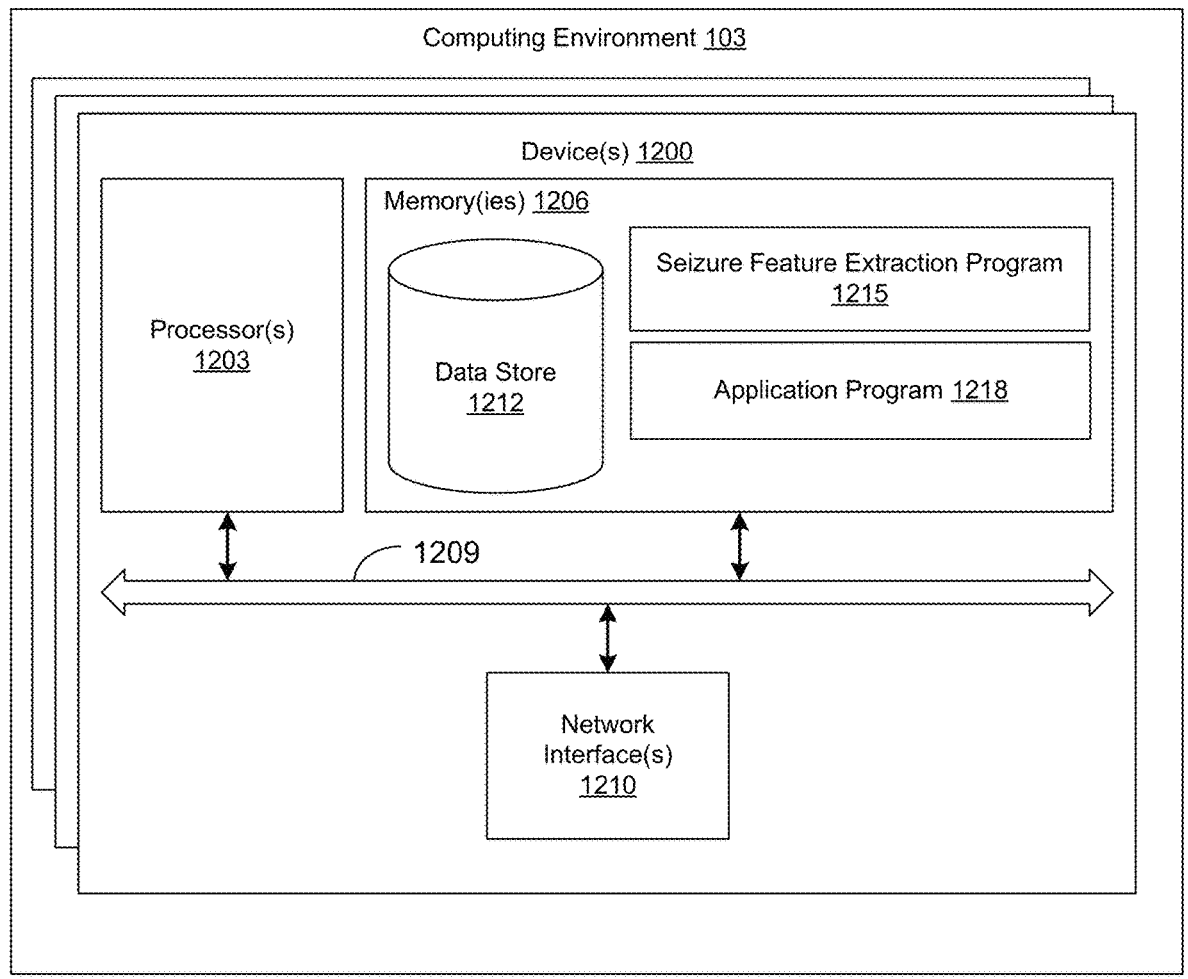
FIG. 12 is a schematic block diagram that provides one example illustration of a computing environment employed in the networked environment of FIG. 1, according to various embodiments of the present disclosure.

With reference to FIG. 12, shown is a schematic block diagram of the computing environment 103 of the ambulatory seizure monitoring system according to an embodiment of the present disclosure. The computing environment 103 includes one or more devices 1200. In some embodiments, among others, the device 1200 may represent a mobile device (e.g. a smartphone, tablet, portable computer, etc.). Each device 1200 includes at least one processor circuit, for example, having a processor 1203 and a memory 1206, both of which are coupled to a local interface 1209. To this end, each device 1200 may comprise, for example, at least one server computer or like device. The local interface 1209 may comprise, for example, a data bus with an accompanying address/control bus or other bus structure as can be appreciated.

In some embodiments, the device 1200 can include one or more network interfaces 1210. The network interface 1210 may comprise, for example, a wireless transmitter, a wireless transceiver, and a wireless receiver. As discussed above, the network interface 1210 can communicate to a remote communication device using a Bluetooth protocol, such as a mobile phone. As one skilled in the art can appreciate, other wireless protocols may be used in the various embodiments of the present disclosure. Additionally, the network interface 1210 may also communicate with a remote communication device in the form of a telephone by placing a telephone call to the telephone, in some embodiments.

Stored in the memory 1206 are both data and several components that are executable by the processor 1203. In particular, stored in the memory 1206 and executable by the processor 1203 are seizure feature extraction program 1215, application program 1218, and potentially other applications. Also stored in the memory 1206 may be a data store 1212 and other data. In addition, an operating system may be stored in the memory 1206 and executable by the processor 1203.

It is understood that there may be other applications that are stored in the memory 1206 and are executable by the processor 1203 as can be appreciated. Where any component discussed herein is implemented in the form of software, any one of a number of programming languages may be employed such as, for example, C, C++, C#, Objective C, Java®, JavaScript®, Perl, PHP, Visual Basic®, Python®, Ruby, or other programming languages.

A number of software components are stored in the memory 1206 and are executable by the processor 1203. In this respect, the term "executable" means a program file that is in a form that can ultimately be run by the processor 1203. Examples of executable programs may be, for example, a compiled program that can be translated into machine code in a format that can be loaded into a random access portion of the memory 1206 and run by the processor 1203, source code that may be expressed in proper format such as object code that is capable of being loaded into a random access portion of the memory 1206 and executed by the processor 1203, or source code that may be interpreted by another executable program to generate instructions in a random access portion of the memory 1206 to be executed by the processor 1203, etc. An executable program may be stored in any portion or component of the memory 1206 including, for example, random access memory (RAM), read-only memory (ROM), hard drive, solid-state drive, USB flash drive, memory card, optical disc such as compact disc (CD) or digital versatile disc (DVD), floppy disk, magnetic tape, or other memory components.

The memory 1206 is defined herein as including both volatile and nonvolatile memory and data storage components. Volatile components are those that do not retain data values upon loss of power. Nonvolatile components are those that retain data upon a loss of power. Thus, the memory 1206 may comprise, for example, random access memory (RAM), read-only memory (ROM), hard disk drives, solid-state drives, USB flash drives, memory cards accessed via a memory card reader, floppy disks accessed via an associated floppy disk drive, optical discs accessed via an optical disc drive, magnetic tapes accessed via an appropriate tape drive, and/or other memory components, or a combination of any two or more of these memory components. In addition, the RAM may comprise, for example, static random access memory (SRAM), dynamic random access memory (DRAM), or magnetic random access memory (MRAM) and other such devices. The ROM may comprise, for example, a programmable read-only memory (PROM), an erasable programmable read-only memory (EPROM), an electrically erasable programmable read-only memory (EEPROM), or other like memory device.

Also, the processor 1203 may represent multiple processors 1203 and/or multiple processor cores and the memory 1206 may represent multiple memories 1206 that operate in parallel processing circuits, respectively. In such a case, the local interface 1209 may be an appropriate network that facilitates communication between any two of the multiple processors 1203, between any processor 1203 and any of the memories 1206, or between any two of the memories 1206, etc. The local interface 1209 may comprise additional systems designed to coordinate this communication, including, for example, performing load balancing. The processor 1203 may be of electrical or of some other available construction.

Although the seizure feature extraction program 1215 and the application program 1218, and other various systems described herein may be embodied in software or code executed by general purpose hardware as discussed above, as an alternative the same may also be embodied in dedicated hardware or a combination of software/general purpose hardware and dedicated hardware. If embodied in dedicated hardware, each can be implemented as a circuit or state machine that employs any one of or a combination of a number of technologies. These technologies may include, but are not limited to, discrete logic circuits having logic gates for implementing various logic functions upon an application of one or more data signals, application specific integrated circuits (ASICs) having appropriate logic gates, field-programmable gate arrays (FPGAs), or other components, etc. Such technologies are generally well known by those skilled in the art and, consequently, are not described in detail herein.

FIG. 1 shows the functionality and operation of an implementation of portions of various embodiments of the present disclosure. If embodied in software, each block may represent a module, segment, or portion of code that comprises program instructions to implement the specified logical function(s). The program instructions may be embodied in the form of source code that comprises human-readable statements written in a programming language or machine code that comprises numerical instructions recognizable by a suitable execution system such as a processor 1203 in a computer system or other system. The machine code may be converted from the source code, etc. If embodied in hardware, each block may represent a circuit or a number of interconnected circuits to implement the specified logical function(s).

Although the FIG. 1 shows a specific order of execution, it is understood that the order of execution may differ from that which is depicted. For example, the order of execution of two or more blocks may be scrambled relative to the order shown. Also, two or more blocks shown in succession in FIG. 1 may be executed concurrently or with partial concurrence. Further, in some embodiments, one or more of the blocks shown in FIG. 1 may be skipped or omitted. In addition, any number of counters, state variables, warning semaphores, or messages might be added to the logical flow described herein, for purposes of enhanced utility, accounting, performance measurement, or providing troubleshooting aids, etc. It is understood that all such variations are within the scope of the present disclosure.

Also, any logic or application described herein, including the seizure feature extraction program 1215 and the application program 1218, that comprises software or code can be embodied in any non-transitory computer-readable medium for use by or in connection with an instruction execution system such as, for example, a processor 1203 in a computer system or other system. In this sense, the logic may comprise, for example, statements including instructions and declarations that can be fetched from the computer-readable medium and executed by the instruction execution system. In the context of the present disclosure, a "computer-readable medium" can be any medium that can contain, store, or maintain the logic or application described herein for use by or in connection with the instruction execution system.

The computer-readable medium can comprise any one of many physical media such as, for example, magnetic, optical, or semiconductor media. More specific examples of a suitable computer-readable medium would include, but are not limited to, magnetic tapes, magnetic floppy diskettes, magnetic hard drives, memory cards, solid-state drives, USB flash drives, or optical discs. Also, the computer-readable medium may be a random access memory (RAM) including, for example, static random access memory (SRAM) and dynamic random access memory (DRAM), or magnetic random access memory (MRAM). In addition, the computer-readable medium may be a read-only memory (ROM), a programmable read-only memory (PROM), an erasable programmable read-only memory (EPROM), an electrically erasable programmable read-only memory (EEPROM), or other type of memory device.

Further, any logic or application described herein, including the seizure feature extraction program 1215 and the application program 1218, may be implemented and structured in a variety of ways. For example, one or more applications described may be implemented as modules or components of a single application. Further, one or more applications described herein may be executed in shared or separate computing devices or a combination thereof. For example, a plurality of the applications described herein may execute in the same device 1200, or in multiple computing devices in the same computing environment 103. Additionally, it is understood that terms such as "application," "service," "system," "device," "module," and "component," and so on may be interchangeable and are not intended to be limiting.

Disjunctive language such as the phrase "at least one of X, Y, or Z," unless specifically stated otherwise, is otherwise understood with the context as used in general to present that an item, term, etc., may be either X, Y, or Z, or any combination thereof (e.g., X, Y, and/or Z). Thus, such disjunctive language is not generally intended to, and should not, imply that certain embodiments require at least one of X, at least one of Y, or at least one of Z to each be present.

It should be emphasized that the above-described embodiments of the present disclosure are merely possible examples of implementations set forth for a clear understanding of the principles of the disclosure. Many variations and modifications may be made to the above-described embodiment(s) without departing substantially from the principles of the disclosure. All such modifications and variations are intended to be included herein within the scope of this disclosure and protected by the following claims.

Therefore, the following is claimed:

1. A system comprising:
   at least one computing device;
   an application executable in the at least one computing device, wherein the application, when executed, causes the at least one computing device to:
   receive a first series of electroencephalograph (EEG) signals from a first sensor and a second corresponding series of EEG signals from a second sensor, the first sensor and the second sensor positioned on a scalp of an individual;
   determine a phase lock value (PLV) based at least in part on the first series of EEG signals and the second corresponding series of EEG signals, wherein the PLV is determined using the exponential power of the differences between a calculated phase of the first series of EEG signals at time t, and a calculated phase of the second series of EEG signals at time t;
   predict an onset of a seizure event for the individual by comparing the PLV with a calculated patient threshold for the individual;
   transmit a notification in response to a seizure prediction horizon indicative of an onset of the seizure event for the individual when the PLV rises above the calculated patient threshold;
   determine an amplitude lock value (ALV) based at least in part on the first series of EEG signals and the second corresponding series of EEG signals, wherein the ALV is determined using the exponential power of the differences between a calculated amplitude of the first series of EEG signals at time t, and a calculated phase of the second series of EEG signals at time, and
   compare the determined ALV with the calculated ALV patient threshold; and
   wherein transmitting the notification further comprises transmitting the notification in response to the comparison of the ALV with the calculated patient ALV threshold to indicate the seizure event when the ALV rises above the calculated patient ALV threshold for a period of time.

2. The system of claim 1, wherein transmitting the notification further comprises transmitting the notification via a wireless transmitter to a remote communication device.

3. The system of claim 1, wherein the comparison indicates that the PLV exceeds the calculated patient threshold for a time period.

4. The system of claim 1, wherein determining the PLV further comprises determining a level of phase synchrony based at least in part on the first series of EEG signals and the second series of EEG signals, the level of phase synchronicity being assigned a value of between 1 for near synchrony and 0 for non-synchrony.

5. The system of claim 1, wherein the calculated patient threshold is based at least in part on previous EEG patient data associated with the individual.

6. The system of claim 1, wherein the first sensor and the second sensor are coupled to a cap worn on the scalp of the individual.

7. The system of claim 1, wherein the notification comprises time interval data determined from prior EEG data from the individual.

8. The system of claim 1, further comprising after the system receives a first series of electroencephalograph (EEG) signals from a first sensor and a second corresponding series of EEG signals from a second sensor, the first sensor and the second sensor positioned on a scalp of an individual, apply a Remez filter to remove spurious noise, apply EEG signal decompose via the Hilbert transformations in order to calculate the phase and amplitude of the signal, and then determine a phase lock value based at least in part on the first series of EEG signals and the second corresponding series of EEG signals.

9. The system of claim 8, wherein the phase is calculated by the arctan(imaginary/real) part of the signal following Hilbert transformations, and the amplitude is calculated by the square root of the sum of the real and imaginary parts of the Hilbert transformation.

10. The system of claim 1, wherein the first sensor and second sensor each comprise dry active electrodes.

11. The system of claim 1, wherein the notification is configured as a text, email, or vibration notification transmitted to a receiver.

12. The system of claim 1, wherein the notification is deemed to be a false positive if not followed by a seizure event within one hour of the notification.

13. A method comprising:
- determining, from previously recorded neurological signals, a calculated patient threshold for an individual that indicates a detection of a seizure event for the individual;
- affixing a plurality of electroencephalograph (EEG) sensors to a scalp of the individual;
- receiving, by at least one computing device, neurological signals from the EEG sensors affixed to the scalp of the individual comprising a first series of electroencephalograph (EEG) signals from a first sensor and a second corresponding series of EEG signals from a second sensor, the first sensor and the second sensor positioned on a scalp of an individual;
- calculating, by the at least one computing device, a phase lock value (PLV) for the neurological signals over a time series;
- calculating, by the at least one computing device, an amplitude lock value (ALV) for the neurological signals over a time series, wherein the amplitude lock value (ALV) is based at least in part on the first series of EEG signals and the second corresponding series of EEG signals, wherein the ALV is determined using the exponential power of the differences between a calculated amplitude of the first series of EEG signals at time t, and a calculated phase of the second series of EEG signals at time;
- comparing, by the at least one computing device, at least the PLV with the calculated patient threshold; and wherein the comparison further includes comparing, by the at least one computing device, at least the ALV with the calculated patient threshold; and
- responsive to the comparison, transmitting, by the at least one computing device, a notification indicating the detection of the seizure event for the individual, wherein transmitting the notification further comprises transmitting the notification in response to the comparison of the ALV with the calculated patient ALV threshold to indicate the seizure event when the ALV rises above the calculated patient ALV threshold for a period of time.

14. The method of claim 13, wherein the calculated patient threshold is identified by locating changes of phase values for the neurological signals.

15. The method of claim 13, wherein the notification is sent when the PLV and ALV exceeds their respective patient threshold.

16. The method of claim 13, wherein the notification is sent when the PLV exceeds the calculated patient threshold and the ALV exceeds the calculated patient threshold.

17. The method of claim 13, wherein the notification indicating the onset of the seizure event for the individual comprises a time interval determined from prior EEG data from the individual.

18. The method of claim 13, wherein after receiving, by at least one computing device, the neurological signals from the EEG sensors affixed to the scalp of the individual, applying EEG signal decompose to the neurological signals using Hilbert transformations and then calculating, by the computing device, the phase lock value for the neurological signals over a time series and the amplitude lock value for the neurological signals over the time series.

19. The method of claim 18, wherein the phase is calculated by the arctan(imaginary/real) part of the signal following Hilbert transformations, and the amplitude is calculated by the square root of the sum of the real and imaginary parts of the Hilbert transformation.

20. The method of claim 13, wherein the plurality of EEG sensors comprise dry active electrodes.

21. The method of claim 13, wherein the PLV is determined using the exponential power of the differences between a calculated phase of the first series of EEG signals at time t, and a calculated phase of the second series of EEG signals at time t, and
wherein the ALV is determined using the exponential power of the differences between a calculated amplitude of the first series of EEG signals at time t, and a calculated phase of the second series of EEG signals at time.

22. The method of claim 13, wherein the notification is configured as a text, email, or vibration notification transmitted to a receiver.

* * * * *